(12) United States Patent
Lee et al.

(10) Patent No.: US 6,214,368 B1
(45) Date of Patent: Apr. 10, 2001

(54) BONE SUBSTITUTION MATERIAL AND A METHOD OF ITS MANUFACTURE

(75) Inventors: Dosuk D. Lee, Brookline, MA (US); Christian Rey, Castanet (FR); Maria Aiolova, Brookline, MA (US)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 08/650,764

(22) Filed: May 20, 1996

Related U.S. Application Data

(63) Continuation-in-part of application No. 08/446,182, filed on May 19, 1995, now Pat. No. 5,650,176.

(51) Int. Cl.$^7$ ...................................... A61K 9/16
(52) U.S. Cl. ...................... 424/423; 424/57; 424/426; 424/484; 424/602; 424/603; 623/16
(58) Field of Search .................... 424/602, 603, 424/57, 423, 426, 484; 523/218, 219; 428/404, 403; 623/16; 106/690, 691, 696; 433/180; 423/308, 311

(56) References Cited

U.S. PATENT DOCUMENTS

| Re. 33,161 | * 2/1990 | Brown et al. ................. 423/308 |
| Re. 33,221 | 5/1990 | Brown et al. ................. 423/308 |
| 4,157,378 | 6/1979 | Tomlinson et al. ............. 423/301 |
| 4,429,691 | 2/1984 | Niwa et al. .................. 128/92 |
| 4,612,053 | 9/1986 | Brown et al. ................. 706/35 |
| 4,684,673 | 8/1987 | Adachi ....................... 523/116 |
| 4,737,411 | 4/1988 | Graves, Jr. et al. ........... 428/403 |
| 4,849,193 | 7/1989 | Palmer et al. ................ 423/308 |
| 4,880,610 | 11/1989 | Constantz ................... 423/305 |
| 4,917,702 | 4/1990 | Scheicher et al. ............. 623/16 |
| 4,938,938 | 7/1990 | Ewers et al. ................. 423/308 |
| 4,959,104 | 9/1990 | Iino et al. .................. 106/85 |
| 5,034,059 | 7/1991 | Constantz .................... 106/161 |
| 5,037,639 | 8/1991 | Tung ......................... 424/57 |
| 5,047,031 | 9/1991 | Constantz .................... 606/77 |
| 5,053,212 | 10/1991 | Constantz et al. ............ 423/305 |
| 5,085,861 | 2/1992 | Gerhart et al. ............... 424/78.17 |
| 5,129,905 | 7/1992 | Constantz .................... 606/76 |
| 5,149,368 | 9/1992 | Liu et al. ................... 424/602 |
| 5,152,836 | 10/1992 | Hirano . |
| 5,164,187 | 11/1992 | Constantz et al. ............ 424/423 |

(List continued on next page.)

FOREIGN PATENT DOCUMENTS

| 0 268 463 | 5/1988 | (EP) . |
| 0 347 028 | 11/1989 | (EP) . |
| 0664133 | 2/1994 | (EP) . |
| 664133 | * 7/1995 | (EP) . |
| 63-111875 | 5/1988 | (JP) . |
| 63-170205 | 7/1988 | (JP) . |
| 2-182261 | 7/1990 | (JP) . |

(List continued on next page.)

OTHER PUBLICATIONS

Costantino et al Hydroxyapatite Cement Arch Otolyaryngol Head Surg vol. 117, pp. 379–384, Apr. 1991.*

(List continued on next page.)

*Primary Examiner*—Neil S. Levy
(74) *Attorney, Agent, or Firm*—Clark & Elbing LLP; Mary Rose Scozzafava

(57) ABSTRACT

The present invention provides a novel process for converting a standard inert amorphous calcium phosphate precipitate into highly reactive amorphous solids. The amorphous solids can be used to react with other calcium phosphate solids to form a poorly-crystalline synthetic hydroxyapatite that provides both bioactivity and structural integrity. This novel amorphous material can be reacted with other calcium phosphates at or below 37° C. to form a bone-like material consisting of poorly crystalline hydroxyapatite.

21 Claims, 10 Drawing Sheets

U.S. PATENT DOCUMENTS

| | | | |
|---|---|---|---|
| 5,178,845 | 1/1993 | Constantz et al. | 423/305 |
| 5,262,166 | 11/1993 | Liu et al. | 424/423 |
| 5,279,831 | 1/1994 | Constantz et al. | 424/423 |
| 5,281,265 | 1/1994 | Liu | 106/35 |
| 5,286,763 | 2/1994 | Gerhart et al. | 514/772 |
| 5,336,264 | 8/1994 | Constantz et al. | 623/16 |
| 5,427,754 | 6/1995 | Nagata et al. | 423/308 |
| 5,470,803 | 11/1995 | Bonfield et al. | 501/1 |
| 5,496,399 | 3/1996 | Ison et al. | 106/35 |
| 5,516,532 | 5/1996 | Atala et al. | 424/548 |
| 5,522,893 | * 6/1996 | Chow et al. | 623/11 |
| 5,525,148 | 6/1996 | Chow et al. | 106/35 |
| 5,542,973 | 8/1996 | Chow et al. | 106/35 |
| 5,545,254 | 8/1996 | Chow et al. | 106/35 |
| 5,562,895 | * 10/1996 | Tung | 424/57 |
| 5,565,502 | 10/1996 | Glimcher et al. | 523/115 |
| 5,605,713 | 2/1997 | Boltong . | |
| 5,650,176 | * 7/1997 | Lee et al. | 424/602 |
| 5,665,120 | 9/1997 | Ohtsuka et al. | 623/16 |
| 5,691,397 | 11/1997 | Glimcher et al. | 523/115 |
| 5,700,289 | 12/1997 | Breitbart et al. | 623/16 |
| 5,782,971 | 7/1998 | Constantz et al. | 106/690 |
| 5,846,312 | * 12/1998 | Ison et al. | 106/690 |

FOREIGN PATENT DOCUMENTS

| | | |
|---|---|---|
| 5-305134 | 7/1993 | (JP) . |
| 06228011 | 12/1994 | (JP) . |
| 7277712 | 10/1995 | (JP) . |
| WO 92/02453 | 7/1991 | (WO) . |
| WO 92/001009 | 1/1992 | (WO) . |
| WO 94/04657 | 8/1993 | (WO) . |
| WO 94/02412 | 2/1994 | (WO) . |
| 9402412 | * 2/1994 | (WO) . |
| WO 94/08458 | 4/1994 | (WO) . |
| WO 94/20064 | 9/1994 | (WO) . |
| WO 95/08319 | 9/1994 | (WO) . |
| WO 94/25080 | 11/1994 | (WO) . |
| WO 94/02412 | 7/1995 | (WO) . |
| WO 96/36562 | 5/1996 | (WO) . |
| WO 97/17285 | 11/1996 | (WO) . |

OTHER PUBLICATIONS

Shindo et al Facial Skeletal Augmentation—Arch. Otolaryngol Head Neck Surg vol. 119, Feb. 1993.*

Appel et al. "Recent Advances in Implants for Bone Growth Promotion" *Exp. Opin. Ther. Patents* 4:1461 (1994).

Athanasou et al., "Current Concepts Review Cellular Biology of Bone–Resorbing Cells" *J. Bone and Joint Surg.* 78A:1096–1112 (1996).

Hayes et al., "Augmentation of Cementless Femoral Stems to Improve Initial Stability Using a Remodelable Calcium–Phosphate Bone Material Substitute" 61$^{st}$ Annual American Academy of Orthopedic Surgeons Meeting, New Orleans (Feb. 1994).

Norian Corporation, Product Information Sheet, "The Material Science of Norian SRS™, Skeletal Repair System™".

Rey et al., "Chemical Properties of Poorly Crystalline Apatites" *Phosphorus Res. Bull.* 6:67–70 (1996) abstract only.

Abboudi et al., "Development of Organic and Polymer Carriers for Demineralized Bone Matrix: Effect on Bone Cell Behavior," Fifth World Biomaterials Congress, May 29–Jun. 2, 1996, Toronto, Canada.

Aoki, "Science and medical applications of hydroxyapatite", JAAS, pp. 11–15, 1991.

Attawia et al., "The Long Term Osteoblast Response to Poly(anhydride–co–imides): A New Degradable Polymer for Use in Bone," Fifth World Biomaterials Congress, May 29–Jun. 2, 1996, Toronto, Canada.

Barton et al., "Surface and bulk properties of amorphous calcium phosphate" Colloid Interface Sci. [Proc. Int. Conf.], 50th 3:71 (1976) [CA 87:73954v] (Abstract).

Besic et al., "Electron probe microanalysis of noncarious enamel and dentin and calcified tissues in mottled teeth", J. Dent. Res., 48:131, (1969).

Blumenthal, et al "Effect of Preparation Conditions on the Properties and Transformation of Amorphous Calcium Phosphate", Mat. Res. Bull. 7 (11):1181 Nov. (1972). Pergamon Press, Inc.

Constantz et al., "Skeletal repair by in situ formation of the mineral phase of bone", Science, 267: 1976 (1995).

Ducheyne et al., "Bioceramic Composites", Chapter 15 from An Introduction to Bioceramics, Advanced Series in Ceramics, vol. 1.

Eanes et al., "Intermediate states in the precipitation of hydroxyapatite", Nature, 208: 365–367 (1965).

Eanes et al., "Intermediate phases in the basic solution preparation of alkaline earth phosphates" Calcified Tissue Res., 2(1):38 (1968) [CA 69:110373f] (Abstract).

Eanes, "Thermochemical studies on amorphous calcium phsophate", Calc. Tiss. Res., 5:133, 1970.

Fenner et al., "High Strength Partially Absorbable Composites Produced by Sintering Method for Internal Bone Fixation," Fifth World Biomaterials Congress, May 29–Jun. 2, 1996, Toronto, Canada.

Gao, T.J. "Established competence of Bioactive Composite Bone Substitute on the Healing of Diaphyseal Segmental Defects in Sheep," Fifth World Biomaterials Congress, May 29–Jun. 2, Toronto, Canada.

Glimcher et al., "Recent studies of the mineral phase in bone and its possible linkage to the organic matrix by protein–bound phosphate bonds", Phil. Trans. R. Soc. Lond., B 304:479–508, 1984.

Glimcher et al., "Recent Studies of Bone Mineral: Is the Amorphous Calcium Phosphate Theory Valid?" J. Crystal Growth, 53: 100–119 (1981).

Graves et al., "Resorbable Ceramic Implants", J. Biomed. Mater. Res. Symposium, No. 2 (Part 1), pp. 91–115 (1971).

Greenfield et al., "Formation chemistry of amorphous calcium phosphates prepared from carbonate containing solutions", Calc. Tiss. Res., 9:152 (1972).

Hirasawa et al., "Manufacture of high purity hydroxyapatite," Chemical Abstracts, 108 (10), p. 166, No. 78193h (Mar. 7, 1988).

Holmes et al., "Surface areas by gas adsorption on amorphous calcium phosphate and crystalline hydroxyapatite", Calc. Tiss. Res., 7:163 (1971).

Ishikawa et al., "Effects of preparation in aqueous solution on properties of hydroxyapatites", Dent. Mater. J. 9(1):58 (1990) [CA 113:218168j] (Abstract).

Jones et al., "Poly [L–Lactide] and Poly [L–Lactide] Ceramic Filled Composites: A Long Term in vivo/in vitro Degradation Study," Fifth World Biomaterials Congress, May 29–Jun. 2, 1996, Toronto, Canada.

Kamei et al., "Implantation of hydroxyapatite–bonded polymer," Fifth World Biomaterials Congress, May 29–Jun. 2, 1996, Toronto, Canada.

Kim et al., "Hyaluronan Based Biodegradable Scaffolds for Skeletal Tissue Reconstruction," Fifth World Biomaterials Congress, May 29–Jun. 2, 1996, Toronto, Canada.

Kinoshita et al., "Reconstruction of Mandibular Discontinuity Defects in Dogs using Autogenic Particulate Cancellous Bone and Marrow and Poly(L–lactide) mesh," Fifth World Biomaterials Congress, May 29–Jun. 2, 1996, Toronto, Canada.

Labarthe et al., "Sur la structure et les properiétés des apatites carbonatées de type B phospho–calciques", Ann. Chem., 8:289 (1973).

Ladizesky et al., "Hydrostatic Extrusion of Hydroxyapatite Polyethylene Composite", Fifth World Biomaterials Congress, May 29–Jun. 2, 1996, Toronto, Canada.

Liu et al., "Nano–Apatite/Polymer Composites II. Surface Modification of Nano–Apatite by Grafting of Polyethylene Glycol," Fifth World Biomaterials Congress, May 29–Jun. 2, 1996, Toronto, Canada.

Nylen et al., "Molecular and ultrastructural studies of non–crystalline calcium phosphates", Calc. Tiss. Res., 9:95 (1972).

Oka et al., "Development of Artificial Osteo–Chondral Composite Material," Fifth World Biomaterials Congress, May 29–Jun. 2, 1996, Toronto, Canada.

Otsuka et al., "Effect of particle size of metastable calcium phosphates on mechanical strength of a novel self–setting bioactive calcium phosphate", J. Biomed Mat. Res., 29:25 (1995).

Pool, "Coral chemistry leads to human bone repair", Science, 269:1772 (Mar., 1995).

Posner et al., "Synthetic amorphous calcium phsophate and its relation to bone mineral structure", Bone Mineral Structure, 8:273–281 (1975).

Rey et al., "The carbonate environment in bone mineral: a resolution–enhanced fourier transform infared spectroscopy study", Calcif. Tissue Int., 45:157 (1989).

Rey et al., "Structural studies of the mineral phase of calcifying cartilage", J. Bone Min. Res., 6:515 (1991).

Rey et al., "Preparation of Microporous Ceramic at Low Temperature from Poorly Crystalline Apatite", Symposium Abstract, 1993.

Rizkalla et al., "Effect of Composition on Strength of Bioactive Composites," Fifth World Biomaterials Congress, May 29–Jun. 2, 1996, Toronto, Canada.

Saifullin, R.S., "Physical Chemistry of Inorganic Polymeric and Composite Materials", Chapter 1: Introduction, Ellis Horwood, New York.

Selmani et al., "Bioerodible Polyester Foams for Orthopaedic Tissue Culture," Fifth World Biomaterials Congress, May 29–Jun. 2, 1996, Toronto, Canada.

Termine et al., "Amorphous/Crystalline Interrelationships in Bone Mineral", Calc. Tiss. Res. 1, 8–23 (1967).

Törmälä, P., "Biodegradable Self–Reinforced Composite Materials; Manufacturing Structure and Mechanical Properties", Clinical Materials 10:29–34 (1992).

Tung et al., "An intermediate state in hydrolysis of amorphous calcium phosphate", Calcif. Tissue Int., 35:783 (1983).

Barton, et al., "Surface and Bulk Properties of Amorphous Calcium Phosphate", Colloid Interface Sci., 50th Proceeding Int'l Conf. 3:71(1976) CA:87:73954v.

Besic, et al., "Electron Probe Microanalysis of Noncarious Enamel and Dentin and Calcified Tissues in Mottled Teeth", J. Dent. Res, 48: 131, Jan.–Feb., 1969.

Constanz, et al., "Skeletal Repair by in Situ Formation of the Mineral Phase of Bone", Science, 267:1976, (Mar., 1995.).

Kinoshita, et al., Reconstruction of Mandibular Discontinuity Defects in Dogs Using Autogenic Particulate Cancellous Bone and Marrow and Poly (L–lactide) Mesh, Fifth World Biomaterials Congress, May 29–Jun. 2, 1996. Toronto, CA.

Labarthe, et al., "Sur La Structure Et Les Proprietes Des Apatites Carbonatees De Type B Phospho–Calciques," Ann Chem. 8:289, 1973.

Nylen, et al., "Molecular and Ultrastructural Studies of Non–Crystalline Calcium Phosphates", Calc. Tiss. Res. 9:95, 1972.

Otsuka, et al., "Effect of Particle Size of Metastable Calcium Phosphates on Mechanical Strength of a Novel Self–Setting Bioactive Calcium Phosphate Cement", Journal of Biomedical Materials Research, 29:25 (1995).

Pool, "Coral Chemistry Leads to Human Bone Repair", Science 269:1772 (Mar., 1995).

Posner, et al., "Synthetic Amorphous Calcium Phosphate and its Relation to Bone Mineral Structure", Bone Mineral Structure,8:273 (1975).

Rey, et al., "Preparation of Microporous Ceramic at Low Temperature From Poorly Crystalline Apatite", Symposium Abstract, 1993.

Rey, et al., "Structural Studies of the Mineral Phase of Calcifying Cartilage", J. Bone Min. Res. 6:515, 1991.

Rey, et al., The Carbonate Environment in Bone Mineral: A Resolution–Enhanced Fourier Transform Infrared Spectroscopy Study, Cal. Tissue Int. 45:157–164, 1989.

Termine, et al., "Amorphous/Crystalline Interrelationships in Bone Mineral", Calc. Tissue. Res.1:8.

Tung, et al., "An Intermediate State in Hydrolysis of Amorphous Calcium Phosphate", Calc. Tissue Int. 35:784, 1983.

Yasue, et al., Effect of Adsorption of Succine Acid on the Formation of Amorphous Calcium Phosphate, International Edition, 102(12):1122(1994).

Driessens, et al., "Calcium Phosphate Bone Cements", Encyclopedic Handbook of Biomaterials and Bioengineering, Wise (Eds) New York, Marcel Dekker, pp 855–877, 1995.

Ducheyne,et al., "Introduction to Bioceramic Composites", Bioceramics, Advanced Series in Ceramics, vol. I.

Eanes, "Thermochemical Studies on Amorphous Calcium Phosphate", Calc. Tiss. Res. 5:133 (1979).

Eanes, et al., "Intermediate Phases in the Basic Solution Preparation of Akaline Earth Phosphates", Calcified Tissue Res. 2(1): 38 (1968).

Eanes, et al., "Intermediate States in the Precipitation of Hydroxyapatite", Nature, 208: 365, (Oct. 1965.).

Fukase, et al., "Setting Reactions and Compressive Strengths of Calcium Phosphate Cements", J. Dent. Res 69(12): 1852, (Dec., 1990).

Gao, et al., Established Competence of Bioactive Composite Bone Substitute on the Healing of Diaphyseal Segmental Defects in Sheep, Fifth World Biomaterials Congress, May 29–Jun. 2, 1996, Toronto, Canada.

Glimcher, "Recent Studies of the Mineral Phase in Bone and its Possible Linkage to the Organic Matrix by Protein–Bound Phosphate Bonds", Phil. Trans. R. Soc. Land. B 304: 479 (1984).

Glimcher, et al. "Recent Studies of Bone Mineral is the Amorphous Calcium Phosphate Theory Valid", Journal of Crystal Growth 53:100 (1981).

Graves, et al., "Resorbable Ceramic Implants", J. Biomed, Mater. Res. Symposium 2:91, (1971).

Greenfield, et al., "Formation Chemistry of Amorphous Calcium Phosphates Prepared from Carbonate Containing Solutions", Calc. Tiss. Res. 9: 152 (1972).

Hollinger, et al., "Role of Bone Substitutes", Clinical Orthopaedics and Related Research, 324: 55, (1996).

Horioglu, et al., "Long Term Follow–up of Hydroxyapatte Cement (HAC) Implants for Craniofacial Reconstruction", 21st Annual Meeting of the Society for Biomaterials, Mar. 18–22, 1995, San Francisco, CA.

Ishikawa, et al., "Effects of Preparation Conditions in Aqueous Solution on Properties of Hydroxyapatites", 9 (1):58 (1990) [CA 113:21868j].

* cited by examiner

BONE SUBSTITUTION MATERIAL AND A METHOD OF ITS MANUFACTURE

This application is a continuation-in-part application of application U.S. Ser. No. 08/446,182 filed May 19, 1995 entitled "Synthesis of Reactive Amorphous Calcium Phosphates" now U.S. Pat. No. 5,650,176.

FIELD OF THE INVENTION

This invention relates to a synthetic poorly-crystalline hydroxyapatite useful as human or animal bone substitution material and for other purposes. The invention further relates to synthesis of amorphous phosphate compounds useful in the formation of poorly-crystalline hydroxyapatite at low temperatures.

BACKGROUND OF THE INVENTION

Calcium phosphates are the principal constituent of hard tissues (bone, cartilage, tooth enamel and dentine). Naturally-occurring bone mineral is made of nanometer-sized, poorly-crystalline calcium phosphate with hydroxyapatite structure. However, unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae, $$Ca_{8.3}(PO_4)_{4.3}(HPO_4, CO_3)_{1.7}(OH, CO_3)_{0.3}$$

Bone mineral non-stoichiometry is primarily due to the presence of divalent ions, such as $CO_3^{2-}$ and $HPO_4^{3-}$, which are substituted for the trivalent $PO_4^{3-}$ ions. Substitution by $HPO_4^{3-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. And because bone tissues undergo constant tissue repair regulated by the mineral-resorbing cells (Osteoclasts) and mineral-producing cells (Osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autogenous bone (patient's own bone) and the risks and complications associated with allograft bone (bone from a cadaver), such as risks of viral transmission. Consequently, there has been considerable attempts to synthesize a ceramic material which closely resembles natural bone for use as implants. Hydroxyapatite is the preferred choice because, although it is a stoichiometric, crystalline form with generally larger crystal sizes, is chemically closest to the naturally occurring mineral in bone.

An ideal synthetic bone graft should possess a minimum of the following four properties: (1) it should be chemically biocompatible like hydroxyapatite; (2) it should provide some degree of structural integrity in order to keep the graft in place and intact until the patient's own bone heals around it; (3) it should be a soluble form to permit resorption so that the patient's own bone replace the foreign hydroxyapatite; and, (4) because it may be necessary to incorporate biomolecules, such as bone growth proteins that can stimulate bone-forming osteoblast cells, into the synthetic bone material, it is desirable that the process used to form the material be carried out at low temperatures. Most bone growth proteins (such as Bone Morphogenetic Proteins) are heat sensitive and lose their bioactivity at temperatures exceeding body temperatures.

Fulfillment of these requirements may be accomplished by a material in which parameters, such as Ca/P ratios, crystal size, crystallinity, porosity, density, thermal stability and material purity are controlled.

The prior art (LeGeros R. Z., in *Calcium Phosphates in Oral Biology and Medicine*, Karger Pub. Co., New York, 1991) teaches that highly crystalline form of hydroxyapatite is produced by solution precipitation followed by sintering at high temperatures (800–1200° C.). High temperature treatment yields highly stoichiometric hydroxyapatite with crystal sizes on the order of several microns with Ca/P of 1.67. Such highly crystalline hydroxyapatite has an extremely low solubility rendering it essentially insoluble in the host tissue. Therefore, it is not replaced by living bone tissue and it remains intact in the patient for an undesirably extended period.

The prior art further teaches that hydroxyapatite is produced by a solid-state acid-base reaction of primarily crystalline calcium phosphate reactants. Such an approach results in materials that are sometimes poorly reacted, inhomogeneous and which have a significant crystalline hydroxyapatite content.

Constantz in U.S. Pat. No. 4,880,610 reports on the preparation of calcium phosphate minerals by the reaction of a highly concentrated phosphoric acid with a calcium source in the presence of a base and hydroxyapatite crystals. The resultant product is a polycrystalline material containing a crystalline form of hydroxyapatite minerals. Likewise, U.S. Pat. No. 5,053,212 to Constantz et al. discloses the use of a powdered acid source to improve the workability and mixability of the acid/base mixture; however, a mixed-phase calcium phosphate material similar to that of U.S. Pat. No. 4,880,610 is reported. Recently, Constantz et al. reported in *Science* (Vol. 267, pp. 1796–9 (Mar. 24, 1995)) the formation of a carbonated apatite from the reaction of monocalcium phosphate monohydrate, Alpha-tricalcium phosphate, and calcium carbonate in a sodium phosphate solution, to provide a calcium phosphate material which is still substantially more crystalline in character than naturally occurring bone minerals.

Similarly, Brown et al. in U.S. Reissue Pat. No. 33,221 report on the reaction of crystalline tetracalcium phosphate (Ca/P of 2.0) with acidic calcium phosphates. Liu et al. in U.S. Pat. No. 5,149,368 discloses the reaction of crystalline calcium phosphate salts with an acidic citrate.

All of these prior art references disclose a chemical reaction resulting in crystalline form of hydroxyapatite solids that has been obtained by reacting crystalline solids of calcium phosphate. There has been little reported on the use of amorphous calcium phosphates (Ca/P of approximately 1.5) as one of the reactants because the amorphous calcium phosphates are the least understood solids among the calcium phosphates and the conventional amorphous calcium phosphate is largely considered to be inert and non-reactive solid.

The only mention of the amorphous calcium phosphate material in prior art has focused on the use of the amorphous calcium phosphate as a direct precursor to the formation of a highly crystalline hydroxyapatite compounds under generally high temperature treatments. Such a highly crystalline material is inappropriate for synthetic bone because it is highly insoluble under physiological conditions.

For example, Palmer et al. in U.S. Pat. No. 4,849,193 report the formation of crystalline hydroxyapatite powder by reacting an acidic calcium phosphate solution with a calcium hydroxide solution, with both solutions near saturation, so as to form an amorphous hydroxyapatite precipitate powder. The amorphous powder is then immediately dried and sintered at high temperature of 700–1100° C. to obtain a very high crystalline hydroxyapatite. Brown et al. in U.S. Reissue Pat. No. 33,221 report on the formation of crystalline hydroxyapatite for dental cement by reacting an amorphous phase specifically restricted to tetracalcium phosphate (Ca/P of 2.0) with at least one of the more acidic calcium phosphates. Further, Brown et al., does not disclose the preparation or the properties of such a tetracalcium phosphate in amorphous state. Tung in U.S. Pat. No. 5,037,639 discloses the use and application of standard amorphous calcium phosphate paste for the remineralization of teeth. Tung proposes the use of standard inert amorphous calcium phosphate mixed with and delivered through as a chewing gum, mouth rinse or toothpaste, which upon entering oral fluids converts to crystalline fluoride containing hydroxyapatite which is useful to remineralize tooth enamel. Simkiss in PCT/GB93/01519 describes the use of inhibitors, such as Mg ions or pyrophosphate, mixed with amorphous calcium phosphate and implanted into living tissues. Upon leaching of, for example Mg ions, into surrounding bodily fluids, the amorphous calcium-magnesium phosphate converts into crystalline hydroxyapatite.

There remains a need to develop new synthetic bone material that more closely mimics the properties of naturally-occurring minerals in bone. In particular, there remains a need to provide synthetic bone materials which are completely bioresorbable, poorly-crystalline, nanometer-sized crystals which can be formed at low temperatures.

SUMMARY OF THE INVENTION

It is an object of the present invention to provide a bone substitute material that is bioresorbable.

It is yet another object of the present invention to provide a bone substitute material which can be formed at low temperatures and which is readily formable and injectable.

It is a further object of the present invention to form a nano-size, poorly-crystalline hydroxyapatite solids with Ca/P ratios comparable to naturally occurring bone minerals.

It is an object of the present invention to provide a process for converting a standard inert amorphous calcium phosphate into a reactive amorphous calcium phosphate.

It is an object of the present invention to provide a reactive amorphous calcium phosphate with surfaces properties that mimic the surface reactivity of naturally-occurring bone mineral.

It is yet another object of the present invention to provide a reactive amorphous calcium phosphate which is capable of forming poorly-crystalline hydroxyapatite at low temperatures (at body temperature of 37° C.).

It is yet a further object of the present invention to provide an injectable calcium phosphate mixture.

In one aspect of the present invention, a method for obtaining a reactive amorphous calcium phosphate is provided. A reactive amorphous calcium phosphate may be prepared by reacting calcium ions, phosphate ions and a third ion, so as to obtain an amorphous calcium phosphate and then removing at least a portion of the third ion, so as to obtain a reactive amorphous calcium phosphate.

By "amorphous" as that term is used here, it is meant a material with significant amorphous character. Significant amorphous character contemplates greater than 75% amorphous content and preferably greater than 90% amorphous content and is characterized by a broad, featureless X-ray diffraction pattern. It is recognized that a small degree of crystallinity may exist in the material, however, it is anticipated, in the case of the amorphous components of the invention, that such crystallinity will not be greater than the degree of crystallinity desired in the product poorly crystalline hydroxyapatitic calcium phosphate. "Reactive" is used herein to refer to the reactivity of the amorphous calcium phosphate of the present invention with other calcium phosphates. The reactivity is characterized by the ability of the amorphous calcium phosphate to harden at 37° C. in less than five hours and substantially harden in about one to five hours in the presence of a calcium phosphate or crystallization promoter. Completeness of reaction, the rate of reaction, homogeneity of the resultant product and ability to react with otherwise inert compounds are characteristic of the reactive ACP of the invention.

In another aspect of the invention includes a reactive amorphous calcium phosphate material having at least 90% percent amorphous character and characterized in that, when prepared 1:1 as a mixture with dicalcium diphosphate in water at 37° C., the mixture hardens within about 10 to about 60 minutes. The invention also includes a reactive amorphous calcium phosphate, obtained by removal of a carbonate pre-component of an amorphous calcium phosphate by thermal decomposition of the pre-component into gaseous or vaporous by-products. The invention still further includes a reactive amorphous calcium phosphate, obtained by removal of a labile component of an amorphous calcium phosphate by thermal decomposition of the component into gaseous or vaporous by-products. The invention yet further still includes a reactive amorphous calcium phosphate material having at least 90% percent amorphous character and characterized in that, when prepared 1:1 as a mixture with dicalcium diphosphate in water at 37° C., the reaction is substantially complete mixture within about 75 minutes, and preferably 40 min.

In another aspect of the invention, a method of preparing a poorly crystalline hydroxyapatite is provided in which the reactive amorphous calcium phosphate of the invention is reacted with a second calcium phosphate. The second calcium phosphate and the reactive amorphous calcium phosphate are mixed in a proportion to form a hydroxyapatitic calcium phosphate.

In another aspect of the invention, a method of preparing a poorly crystalline hydroxyapatite is provided in which the reactive amorphous calcium phosphate of the invention is reacted with a promoter. The promoter selected to convert the reactive amorphous calcium phosphate into a hydroxyapatitic calcium phosphate.

Another aspect of the invention includes a resorbable bone substitute material comprising a poorly crystalline hydroxyapatite having an X-ray diffraction pattern substantially as shown in FIG. 7d. The invention also includes a resorbable bone substitute material comprising a poorly crystalline hydroxyapatite having an X-ray diffraction pattern comprising broad peaks at 2θ values of 26°, 28.5°, 32° and 33°. The invention further includes a resorbable bone substitute material comprising a poorly crystalline hydroxyapatite, characterized in that, when placed in a rat intramuscular site, resorption of at least 100 mg, and preferably 300 mg, of the bone substitute material is complete within one month.

The resorbable bone substitute material is further characterized in that, when prepared from a reaction of amorphous calcium phosphate and a second phosphate in a fluid, the reaction mixture hardens after a time greater than 60 minutes at about 22° C., and the reaction mixture hardens within about 10 to 60 minutes at 37° C. In preferred embodiments, the mixture is injectable for a time greater than about 60 minutes at about 22° C. In other preferred embodiments, the mixture is formable for a time greater than about 60 minutes at about 22° C.

Another aspect of the invention, includes a formable paste, suitable for use as a resorbable bone substitution material. The paste includes a mixture of the reactive amorphous calcium phosphate of the invention, and a second calcium phosphate powder; and an amount of a fluid sufficient to provide the desired consistency, said mixture capable of hardening at about 22° C.

The paste of the invention may also include a mixture of the reactive amorphous calcium phosphate of the invention, and a promoter, the promoter selected to convert the reactive amorphous calcium phosphate into a hydroxyapatitic calcium phosphate; and an amount of a fluid sufficient to provide the desired consistency, said mixture capable of hardening at about 22° C.

In preferred embodiments, the mixture hardens after a time greater than 60 minutes at about 22° C., and wherein the mixture hardens within about 10 to 60 minutes at about 37° C.

BRIEF DESCRIPTION OF THE DRAWINGS

A description of the invention is made with reference to the figures in which.

DETAILED DESCRIPTION OF THE INVENTION

Figure 1:
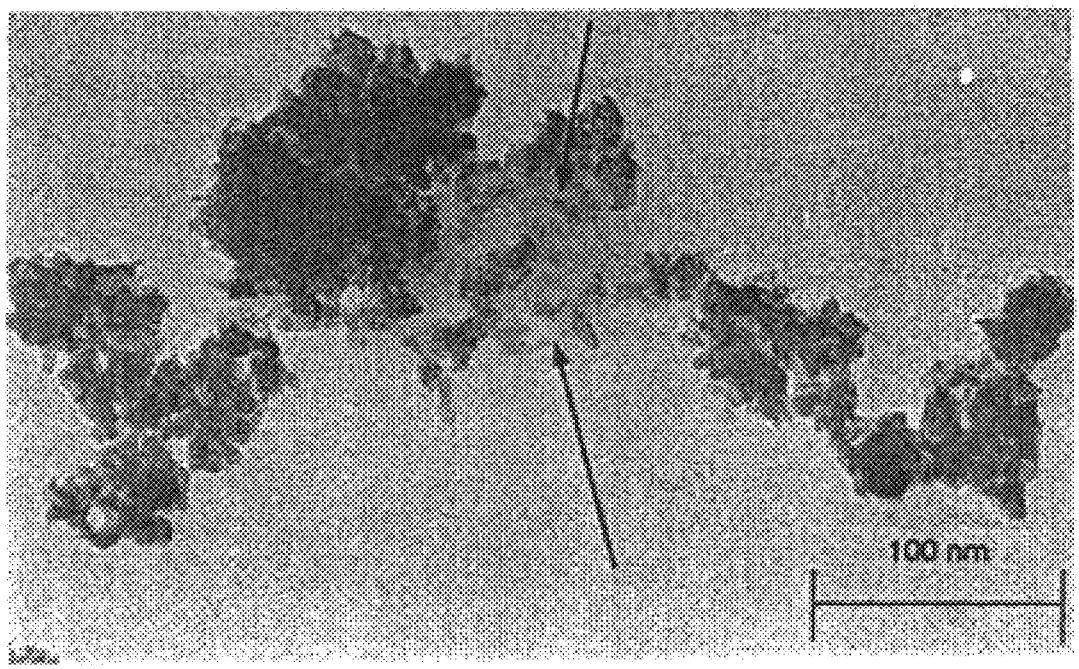
FIG. 1 is a high-resolution transmission electron micrograph of the reactive amorphous calcium phosphate illustrating the nanometer-sized grains in clusters with relatively unclear boundaries and partially immersed in shapeless form (arrows)

The current invention provides a fully resorbable and reossifying poorly crystalline hydroxyapatite (HA) useful as a bone substitute material (BSM) for the treatment of bone disorders and injuries and other biological applications requiring resorbable calcium phosphate. The poorly crystalline HA of the invention is characterized by its biological resorbability and its minimal crystallinity. It may be highly porous and rapidly resorbable or of decreased porosity and slowly resorbable. Its crystalline character is substantially the same as natural bone, without the higher degree of crystallinity seen in the bone substitute materials known to the art. The inventive poorly crystalline HA also is biocompatible and not detrimental to the host.

In an important aspect of the invention, the ease of use of the poorly crystalline HA in a surgical setting is significantly improved over other bone substitute materials known in the art. Specifically, the reaction is initiated outside the body and proceeds slowly at room temperature thereby minimizing any possibility that the material will "set up" prior to application to the surgical site and become unusable. The reaction accelerates significantly at body temperature and the material hardens in place. Furthermore, the consistency and formability of the poorly crystalline HA as well as the reaction speed may be varied according to the therapeutic need, by modifying a few simple parameters.

The resorbability of the bone substitute material of the instant invention is attributable to the combination of its porosity and significant amorphous character. The bone substitute material of the invention comprises a poorly crystalline hydroxyapatitic calcium phosphate, substantially similar to that found in natural bone. Lack of crystallinity in apatites is associated with somewhat increased solubility in aqueous systems compared to other more crystalline species, thus the low crystallinity and/or presence of stably amorphous apatitic domains is believed to promote resorbability in biological systems. Porosity facilitates both the penetration of cells and cell processes into the bone substitute material matrix and the diffusion of substances to and from the matrix interior. Accordingly, bone substitute materials of lower porosity resorb more slowly in vivo than those of high porosity.

In preferred embodiments, the reactants are mixed outside of the body, yielding a formable bone substitute material suitable for application to a surgical site. The reaction generally is completed after application to the surgical site. Bone substitute materials of the invention generally harden in less than five hours and substantially harden in about one to five hours under physiological conditions, and preferably in about 10–30 minutes. In a preferred embodiment, the reaction is initiated by adding distilled water to a mixture of two dry components to form a thick paste which hardens in about a half an hour. Other aqueous agents such as serum or tissue culture medium may be used in place of distilled water. Most often the resulting resorbable poorly crystalline hydroxyapatite will be calcium deficient with a calcium to phosphate ratio of less than 1.5 as compared to the ideal stoichiometric value of approximately 1.67 for hydroxyapatite.

The invention also provides a test for identifying suitable reactive bone substitute materials and reactive precursors. The test comprises combining the components, producing a formable substance and demonstrating its ability to harden in a suitable amount of time at or around body temperature. Components which harden in this way may then be placed intramuscularly in a test animal and checked for biological resorbability. One hundred milligrams (100 mg), and preferably three hundred milligrams (300 mg), of a bone substitute material of the present invention will resorb in less than 1 month in a rat muscle. Some more slowly resorbable bone substitute materials may require more than a year for complete resorbtion in rodents.

The bone substitute material formation reaction employs at least one amorphous calcium phosphate (ACP) precursor, and preferably employs an activated ACP. In some instances, the reaction may employ only one precursor ACP which is converted in a controlled fashion in part or whole to the poorly crystalline HA (bone substitute material) of the invention. Alternatively, the reaction may employ one or more additional precursors preferably a calcium and/or a phosphate source, which combine with the ACP to yield the poorly crystalline hydroxyapatite of the invention. In any event, reactions which can be initiated outside of the body, carried on in a paste-like configuration and which significantly accelerate at 37° C. leading to a hardened calcium phosphate product are greatly preferred.

ACP Precursors Only

When amorphous calcium phosphate is used as the sole precursor to produce a resorbable bone substitute material, it is important to control the natural tendency of the ACP to convert to highly crystalline hydroxyapatite. On the other hand, the time course of conversion should be fast enough to have surgical utility. One approach is to combine a precursor ACP containing an inhibitor of crystal formation (e.g. the ACP of example 1) with an ACP that does not contain an inhibitor of crystal formation (e.g., a promoter). The reactants may be mixed in a dry state, with the appropriate particulate size and an excess of the inhibitor-containing ACP. The reactants can then be exposed to crystal-forming conditions such as the addition of water, followed by an elevation in temperature, such as that which occurs following introduction into the body, to convert the reactants to the poorly crystalline HA of the invention.

ACP Precursor Plus Additional Calcium Phosphate Sources

ACP may be reacted with a second calcium source (including a second ACP) using any reaction promoting technique. The reaction being promoted is the conversion of an amorphous calcium phosphate into a nanocrystalline or poorly crystalline hydroxyapatite. Such reactions include acid/base, displacement, substitution, and hydrolysis reactions as well as purely physical and mechanical reactions (e.g., grinding, mixing). Under any reaction scheme it is important that the ACP retains significant amorphous character throughout the reaction. Specifically, the overall crystallinity within the starting product cannot exceed that desired in the end product. Thus certain reaction schemes may require stabilization of the amorphous nature of the ACP throughout the reaction period. Examples of suitable such inhibitors of crystal formation known to the art include carbonate, fluoride, and magnesium.

In many forms of the current invention, at least one of the precursors must be activated so as to react with the other components at physiological conditions. In some preferred embodiments the ACP component is activated under heat in order to facilitate the reaction with the second calcium containing reactant. Examples of suitable such second reactants include DCPD, other crystalline or poorly crystalline calcium phosphates, calcium sources or phosphate sources, or a second ACP. Other methods of activation known to the art such catalysis or the use of ionic solvents may also be used to promote reaction between substituents. The second calcium phosphate reactant may be of any crystalline structure and should be chosen so as to be reactive with the first ACP either directly or through the use of a reaction promoting vehicles such as ionic solvents. Appropriate reaction conditions will be determined by demonstration of rapid hardening at 37° C., following mixing of the reactants and the addition of water.

The bone substitute material forming reaction may also be designed to produce an end product that is porous. In one embodiment, the principles of acid/base chemistry plus the use of a dry mixture of controlled particle size reactants leads to a porous bone substitute material. Other methods of promoting porosity such as chemical or physical etching and leaching may be employed.

The present invention provides a novel process for converting a standard inert amorphous calcium phosphate precipitate into highly reactive amorphous solids. The amorphous solids can be used in the reactions described above to form a poorly- or nano-crystalline synthetic hydroxyapatite that provides bioactivity, bioresorbability and structural integrity. This novel amorphous material can be reacted with other calcium phosphates at or below 37° C. to form a bone-like material consisting of poorly crystalline hydroxyapatite.

The amorphous calcium phosphate of the present invention is highly reactive 30 towards other acidic or basic calcium phosphates. Also, the amorphous calcium phosphate of the present invention is considered reactive in that it is capable of reacting at room temperature with a variety of calcium- or phosphorus-bearing compounds which are conventionally considered "inert" to ACP, for example CaO, $CaCO_3$ and calcium acetate. Prior art acid-base reactions of conventional crystalline calcium phosphate results in poorly reacted solids, having reaction product that are too crystalline to be sufficiently soluble in a living tissues. The reactions from the prior art are generally incomplete and the reaction products are inhomogeneous. In contrast, the amorphous calcium phosphate of the present invention reacts quickly and completely with a wide variety of calcium phosphates and other calcium- or phosphorus-bearing materials to provide a homogeneous product.

The source of the enhanced reactivity is not completely understood; however, it is believed to be associated with the amorphicity (lack of crystallinity) and, in some embodiments, site vacancies in the material, as created by the process of the present invention. The vacancies may provide reactive sites for subsequent reaction. These observations will be discussed more fully, below.

The method of the present invention permits initial formation of amorphous calcium phosphate particles of less than 1000 Å, preferably 200–500 Å, and most preferably 300 Å, the further growth of which are curtailed by rapid precipitation of the product from solution. During reaction of calcium and phosphate ion sources to form an amorphous calcium phosphate, a third ion is introduced in the solution so that these ions are incorporated in the amorphous precipitate structure instead of trivalent $PO_4^{3-}$ group(s). Because some $PO_4^{3-}$ is replaced by the third ion, the overall $PO_4^{3-}$ decreases, thus increasing the Ca/P ratio of the amorphous precipitate (as compared to standard amorphous calcium phosphate) and modifying the valence or charge state of the calcium phosphate. The amorphous solids then may be rapidly freeze-dried to preserve the chemical and physical properties of the material. The amorphous solids then may be treated under specific conditions selected to promote removal of at least some of the third ion. In the case of carbonate, specific temperature and pressure conditions lead to the reduction of total carbon, presumably as gaseous carbon dioxide and oxygen from the amorphous solid, while maintaining the amorphicity.

The resultant material is an amorphous solid with a higher Ca/P ratio than is typically found in amorphous calcium phosphates, which is generally reported in the past to be 1.50. Further, removing carbon from the material results in a vacancies in the interstitial structure within the amorphous solids, rendering it a highly reactive solid. There may be several possible vacancies sources. The material possesses a porosity which promotes reactivity by various means, such as increased surface area. The material may also undergo a change in the stoichiometry balance upon removal of the third ion. This stoichiometry change may result a charge imbalance which is responsible for the increased reactivity of the amorphous calcium phosphate.

It is desirable to maintain the amorphous property of the material throughout the entire process. If crystallinity in its entirety (single crystalline regions) or even in local domains (microcrystalline regions) is introduced during the process or in the final product, the solid has been found to lose its reactivity. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

The amorphous state is induced by controlling the rate and duration of the precipitation process. The amorphous hydroxyapatite of the present invention is precipitated from solution under conditions where initial precipitation is rapid. Rapid precipitation results in the formation of many extremely small calcium phosphate nuclei. Additionally, rapid crystal or grain growth leads to the production of more defects within each grain, thereby also increasing solubility. At the extreme end of the spectrum, crystal or grain growth is so rapid and defect density is so significant that an amorphous calcium phosphate results. Amorphous calcium phosphate is gel-like and includes solid solutions with variable compositions. These gels have no long range structure, but are homogeneous when measured on an Angstrom scale. Under physiological conditions, these amorphous compounds have high solubilities, high formation rates and high rates of conversion to poorly crystalline hydroxyapatite.

The amorphous calcium phosphate solids acquired by this method retain their amorphous nature sufficiently long enough to be introduced into the final reaction as substantially amorphous solids. They can also be mixed and reacted with other solids or solutions containing phosphates, to obtain solids containing a homogeneous distribution of nanometer-sized crystals. Further in preferred embodiments, because the amorphous calcium phosphate reacts completely with the other solids, the Ca/P of the resultant solid will constitute the total calcium and phosphorous from such reaction, i.e., there will be an essentially complete reaction. When a proper molar concentration of phosphate from the solution or solids is reacted with the novel amorphous calcium phosphate material, a poorly crystalline hydroxyapatite material (Ca/P 1.1–1.9) is obtained. Thus, the present invention permits one to design and modify the chemical composition of the resultant product, thereby providing a further mode of controlling bioactivity of the final product used as bone graft material.

In one embodiment of the present invention, a solution is prepared which contains calcium and phosphate ions and a third ion in a concentration, at a pH and at a temperature which will promote the rapid nucleation and precipitation of calcium phosphate. When precipitation is sufficiently rapid, an amorphous gel-like calcium phosphate is formed. Because the thermodynamically favored crystalline form of hydroxyapatite is enhanced by reducing the rate of reaction, certain processing steps of increasing the rate of reaction may be taken to ensure that an amorphous compound is obtained. The following factors, among others, are to be considered when designing a solution for the rapid precipitation of the amorphous calcium phosphate of the present invention.

Preferred conditions: Rapid mixture of calcium and phosphate sources to increase the rate of reaction. The rate of reaction is increased to favor non-stable phases as a product. Allowing more reaction time for each of the ions to juxtapose correctly to form a solid will result in a more thermodynamically favorable crystalline and stable structure.

Preferred calcium and phosphate sources: The use of highly concentrated or near supersaturation solutions ensures that a more rapid reaction will occur.

Preferred temperature: Although the reaction can be carried out at room temperature, temperatures of near boiling point to increase the concentration of one reactant is a possible means of increasing the rate of reaction.

In one embodiment, an aqueous solution of calcium ions, phosphate ions and carbonate ions are mixed together rapidly to obtain a carbonate containing amorphous calcium phosphate solid. The relative concentrations of the ions are selected to give a precipitate having the desired Ca/P ratio. The carbonate ion substitutes for a phosphate ion in the amorphous calcium phosphate. The carbonated amorphous calcium phosphate may be obtained by precipitation from an aqueous carbonate solution. Suitable aqueous carbonate solutions include, by way of example only, bicarbonate solution, sodium carbonate solution, potassium carbonate solution. It is further contemplated as within the scope of the invention to use non-aqueous solutions.

Use of a carbonated material is desirable because it permits manipulation of the Ca/P ratio by substitution of $PO_4^{3-}$ by $CO_3^{2-}$. Additionally, the presence of $CO_3^{2-}$ is known to retard the development of crystallinity in amorphous calcium phosphate. Is recognized, however, that other ions or a mixture of ions may be suitable in place of or in addition to carbonate ion in modifying the Ca/P ratio and in introduction of reactive site vacancies into the amorphous calcium phosphate, such as by way of example only, nitrate, nitrite, acetate, $Mg^{+2}$ and $P_2O_7^{4-}$ ions.

The amorphous calcium phosphate precipitate may be collected and filtered prior to activation. It is preferred to perform this step in a cold room or at sub-ambient temperatures so as to preserve the amorphous state of the precipitate collected. Collection may typically may be carried out by any conventional means, including, but in no way limited to gravity filtration, vacuum filtration or centrifugation. The collected precipitate is gelatinous and is washed more than once with distilled water.

The washed precipitate is then dried under any conditions which maintain the amorphous character of the material. Lyophilization is a suitable, but not exclusive, technique. Upon freezing, the precipitate while kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^{-1}$–$10^{-4}$, preferably $10^{-2}$, torr. A preferred method includes lyophilization because the cryogenic temperatures typically used in lyophilization inhibit further crystallization of the material. As a result, the amorphous calcium phosphate obtained thereby is an extremely fine free flowing powder.

The dried ACP may then be activated. In a preferred embodiment, where carbonate is present in the ACP, the ACP powder is heated to drive off remaining free water, water of hydration and to remove carbon, presumably through the decomposition of $CO_3^{2-}$ into $CO_2$ and oxygen. The heating step is carried out at a temperature of less than 500° C. but more than 425° C., so as to prevent conversion of the amorphous calcium phosphate into crystalline hydroxyapatite. Heating is preferably carried out at a temperature in the range of 450–460° C. In a preferred embodiment, the freeze-dried amorphous calcium phosphate powder is heated under vacuum. In a vacuum environment, the temperature may be considerably less, i.e., in the range of about 175–225° C., to obtain the same result. The lower temperatures may be desirable because they reduce the risk of crystallization of the amorphous powder.

Low crystallinity and site vacancies (porosity and/or stoichiometric changes) may account for the observed higher reactivity of the amorphous calcium phosphate of the present invention. This is exemplified by the following observations. A carbonate-containing amorphous calcium phosphate which has been heated to 525° C. is observed to have an increase in formation of crystalline hydroxyapatite and to have a corresponding decrease in reactivity. Amorphous calcium phosphate that is heated to only 400° C. retains its amorphous characteristic, but exhibits a decreased reactivity. Presumably this decrease in reactivity is related to the higher carbonate levels (and less site vacancies) observed by IR in samples treated at this lower temperature. This suggests that both amorphicity and decreased carbon content (vacant reactive sites) are a factor in reactivity. This is not intended to be in any way an exclusive basis for reactivity. Other basis for the observed reactivity are considered to be within the scope of the invention. The resulting amorphous calcium phosphate powder is a highly reactive amorphous calcium phosphate material with a Ca/P ratio of between 1.1–1.9, preferably about 1.55 to 1.65, and most preferably about 1.58. The powder has been characterized by a variety of analytical techniques.

Figure 2A:
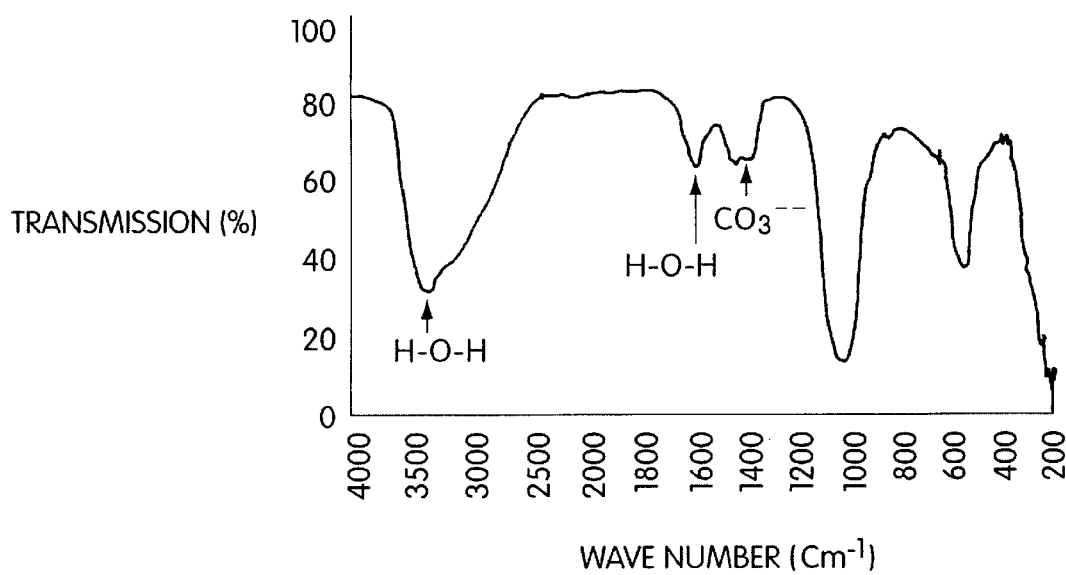
FIG. 2 is an infrared spectrum of the reactive amorphous calcium phosphate of the present invention (a) prior to and (b) after heating step. Note the disappearance of H—O—H group (~3,550 $cm^{-1}$ and 1,640 $cm^{-1}$) and $CO_3^{2-}$ group (1420–1450 $cm^{-1}$) after heat treatment.
Figure 2B:
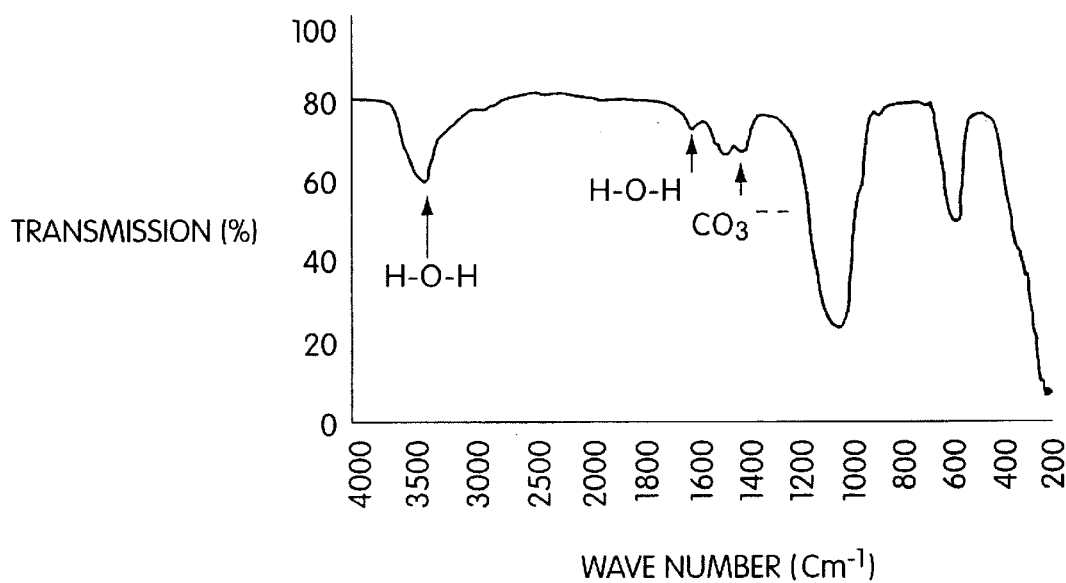
Figure 3A:
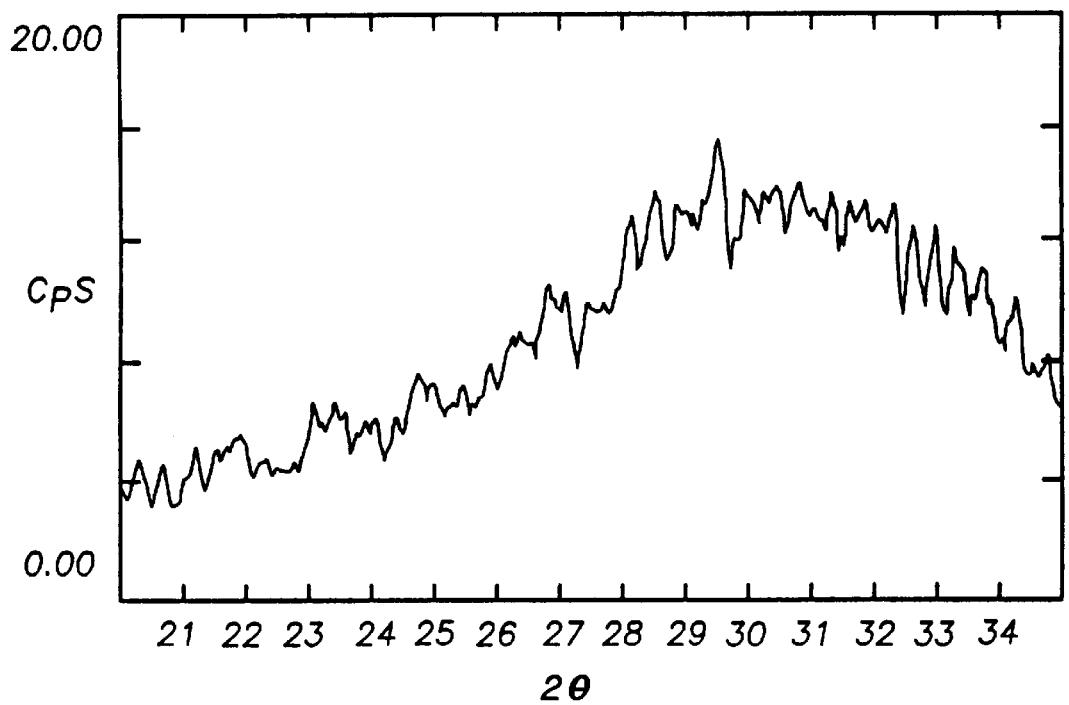
FIG. 3 is an x-ray diffraction pattern of the reactive amorphous calcium phosphate of the present invention (a) prior to and (b) after the vacuum heating step. The material is showing the preservation of the amorphous state after the vacuum heat treatment. It is characterized by absence of sharp peaks and broad maxima between 20° and 35° diffraction angle. The amorphous state of the solids is maintained throughout the entire process of the present invention.
Figure 3B:
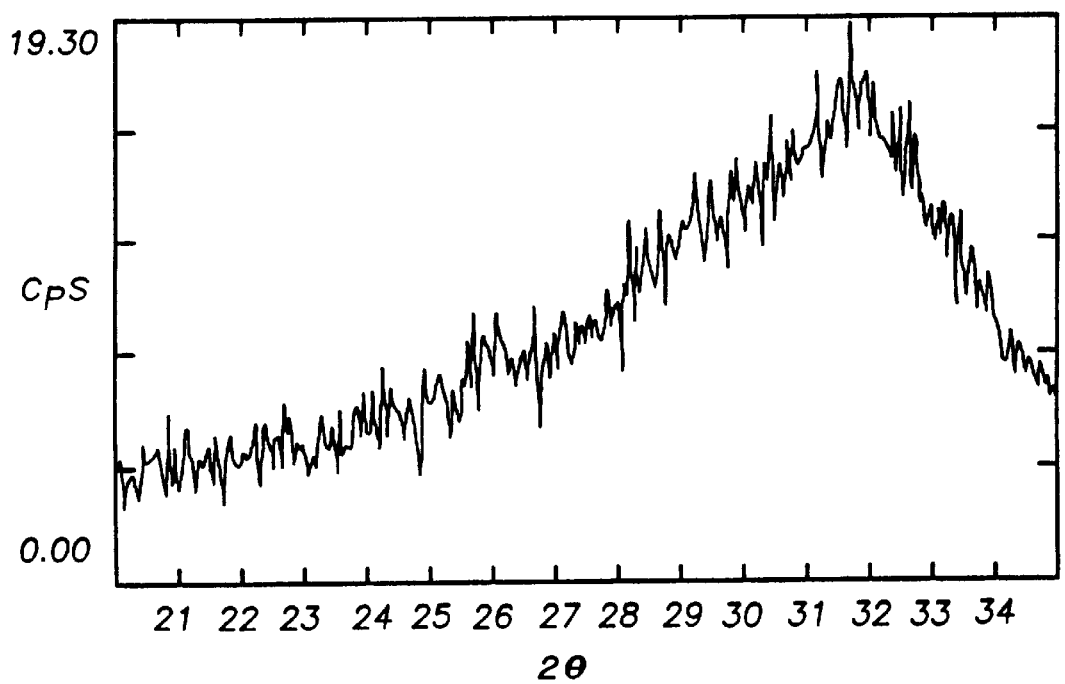
Figure 4:
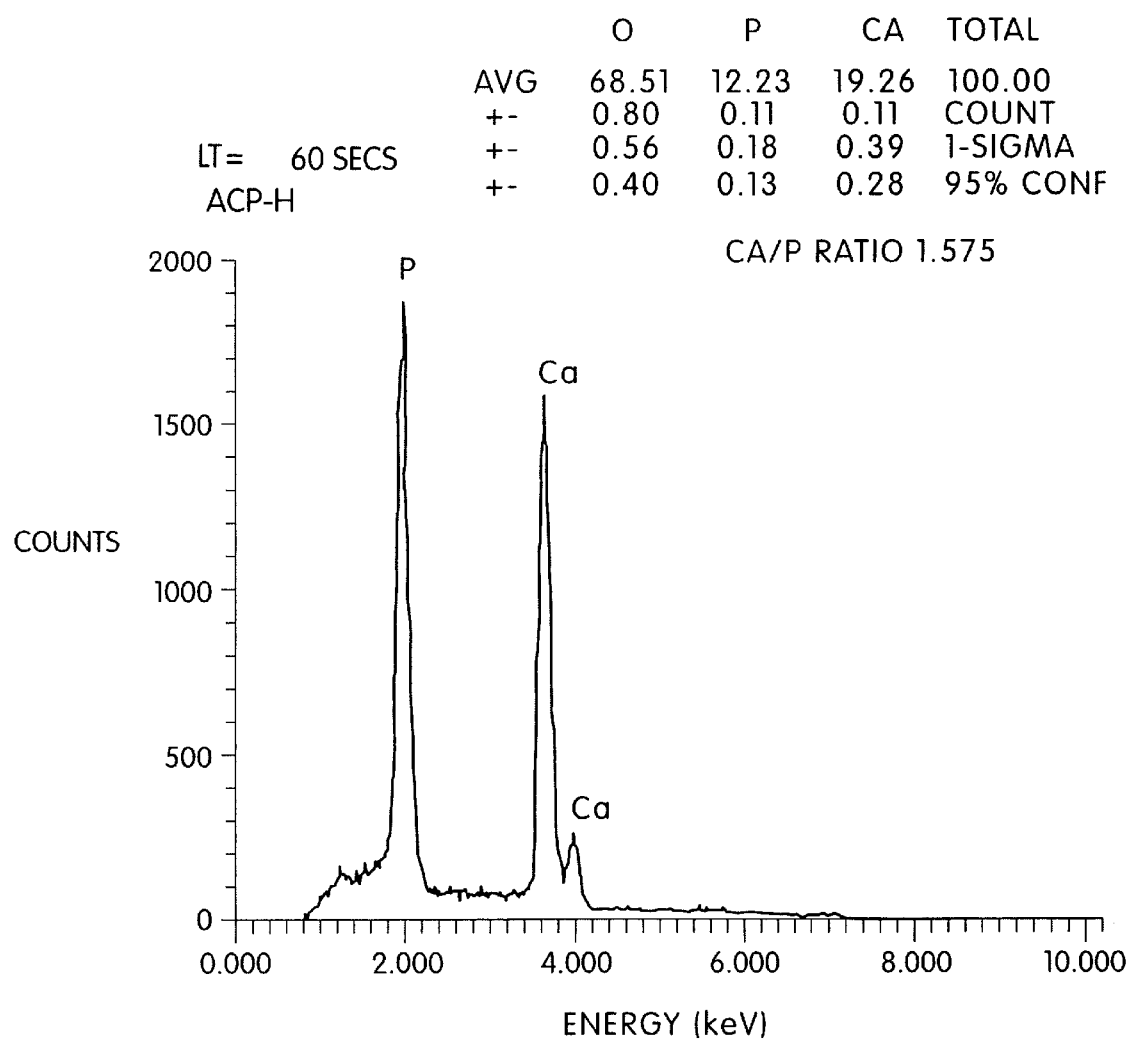
FIG. 4 is an energy-dispersive electron microprobe spectrum of the reactive amorphous calcium phosphate of the present invention after the vacuum heating procedure which yielded Ca/P to be 1.58.

In FIG. 1, a high-resolution transmission electron micrograph is shown to illustrate the morphological characteristics and the angstrom-sized nature of the preferred reactive amorphous calcium phosphate of the present invention. Preferred particle sizes are less than 1,000 Å, preferably in the range of 300–400 Å. Note the unclear boundaries separating the globule-like clusters, lacking clear edges and surfaces, in contrast to crystalline materials. FIG. 2a and 2b illustrate infrared spectra of the amorphous calcium phosphate after lyophilization process (a) and after the subsequent heat treatment at 450° C. for 1 hr (b). Infrared peaks illustrating presence of local chemical groups in the material show that the presence of H—O—H (at approximately 3,400 $cm^{-1}$ and 1640 $cm^{-1}$) and $CO_3^{2-}$ group (at 1420–1450 $cm^{-1}$) are significantly reduced after heat treatment. However, the x-ray diffraction patterns in FIG. 3 of similar materials show that the amorphous state after the lyophilization (a) is substantially unchanged after the heat treatment (b). The amorphous nature of the present invention material is characterized by broad peaks and undefined background with absence of sharp peaks at any position of the diffracting angles that correspond to known crystalline calcium phosphates. The Ca/P measurement performed using wave length-dispersive X-ray analysis on an electron micro-probe of the same material after heat treatment yields Ca/P to be 1.58 (FIG. 4).

These characterizations demonstrate that although there is a change in the local moiety of certain groups in the amorphous calcium phosphate solids, the overall amorphicity is maintained throughout the process. Thus allowing an interpretation of the material to contain local vacancies or "holes" in the amorphous structure which may activate the ACP.

In another preferred embodiment, the highly reactive amorphous calcium phosphate is reacted with an acidic or basic calcium phosphate to obtain a poorly crystalline hydroxyapatite. As discussed above, hydroxyapatite is the thermodynamically preferred reaction product which readily crystallizes to give a product that is not biocompatible due to its insolubility under physiological conditions. The use of an amorphous calcium phosphate, which can react quickly and completely to a product hydroxyapatite without significant crystallization, provides a novel route to a poorly-crystalline hydroxyapatite which is resorbable under physiological conditions.

The amorphous calcium phosphate powder of the present invention may be mixed with a variety of second components to thereby react to form a poorly crystalline form of hydroxyapatite. This reaction occurs at room temperature upon mixing of the powder with a variety of both acidic and basic calcium phosphates in the presence of a fluid, such as but not limited to, water, saline, buffer solution, serum or tissue culture medium. Depending upon the amount of fluid added the mixture of amorphous calcium phosphate of the present invention and acidic calcium phosphate results in a highly formable and/or highly injectable paste with varying degrees of paste consistency.

Appropriate calcium phosphates include both basic and acidic calcium phosphates which provide the appropriate stoichiometry for reaction to obtain a hydroxyapatitic calcium phosphate. In a preferred embodiment, an acidic (pH 5–7) calcium phosphate is used. Suitable acidic calcium phosphates include, but are in no way limited to, calcium metaphosphate, dicalcium phosphate dihydrate, heptacalcium phosphate, tricalcium phosphates, calcium pyrophosphate dihydrate, poorly crystalline HA, calcium pyrophosphate, and octacalcium phosphate. Suitable basic calcium phosphates include additional ACPs. Other solids which would provide a source of phosphate or calcium, such as by way of example only, CaO, $CaCO_3$, calcium acetate, and $H_3PO_4$, may be mixed to form a final product to yield a desired Ca/P ratio close to natural bone. It may be desirable to provide the second component in the amorphous or poorly crystalline state, as well.

Hydroxyapatite is a thermodynamically favored form of calcium phosphate. It is therefore within the scope of the invention to merely promote the conversion of the reactive ACP into a poorly crystalline HA, by addition of components which promote conversion of ACP into HA, without chemical reaction. Suitable promoters include, but are not limited to, water and heat.

Figure 6A:
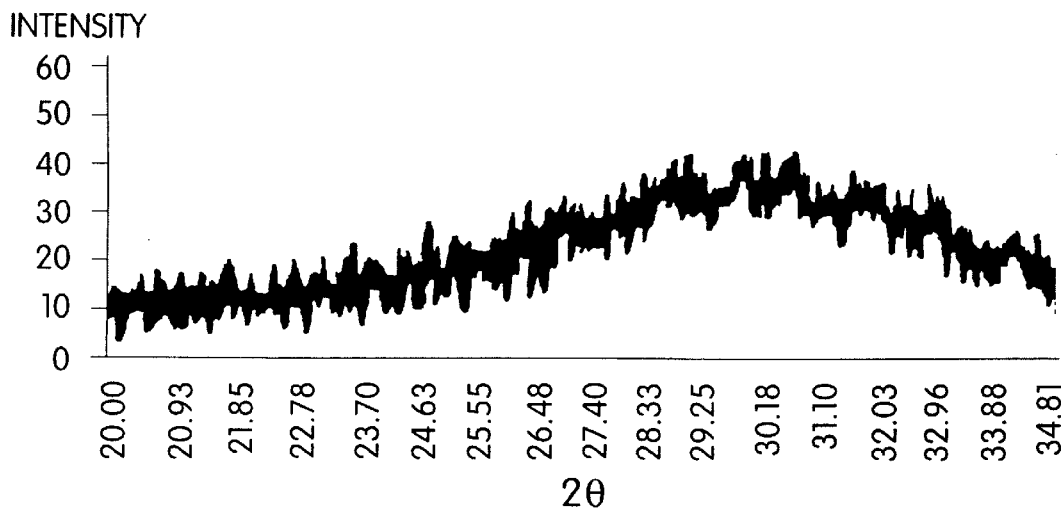
FIG. 6 are X-ray diffraction patterns of (a) reactive amorphous calcium phosphate; and (b) dicalcium diphosphate used in a reaction to form a bone substitute material of the invention.
Figure 6B:
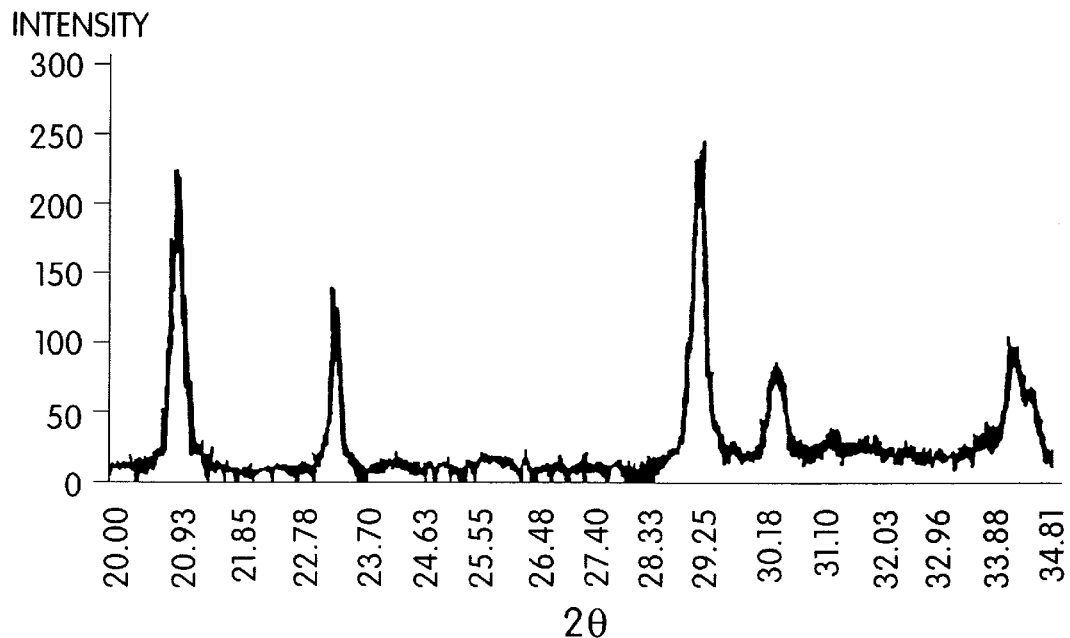

The second calcium phosphate is often crystalline, as is evidenced by the presence of sharp diffraction peaks typical to the calcium phosphate of interest in the X-ray diffraction pattern (FIG. 6a). In contrast, the reactive ACP is amorphous and shows no identifiable peaks by X-ray diffraction (FIG. 6b). Despite its higher crystallinity, however, dicalcium diphosphate is consumed in the reaction with reactive ACP and the product HA is of much reduced crystallinity.

Because at least one of the reactants is amorphous and highly reactive, the reaction proceeds at room temperature to provide an apatitic material having a poorly-crystalline or microcrystalline microstructure. The reaction also is substantially complete, thereby insuring that all calcium and phosphate of the mixture are consumed by the resultant hydroxyapatite product. This permits reliable manufacture of hydroxyapatite products simply by selection of the relative proportions of the starting amorphous and secondary calcium phosphates. It is desirable to maintain a calcium to phosphate ratio of about 1.2–1.68, preferably less than 1.5, and most preferably about 1.38.

The product hydroxyapatite material contains labile environments characteristic of naturally-occurring bone. In naturally occurring bone, minerals are characterized by nanometer-sized structure, providing high surface areas to interact with the surrounding tissue environment, resulting in resorption and remodelling of tissues. The present invention, with its nanometer-sized crystals as the product, closely mimics the naturally occurring bone minerals. Further, properties such as crystallinity and Ca/P ratios are closely designed in the present invention to simulate the mineral properties found in living tissues of bone.

In another preferred embodiment, an injectable paste may be prepared, which can be introduced into the bone repair site. The paste is generally prepared by mixture of the amorphous calcium phosphate of the present invention with a second component in an amount of water or buffer sufficient to produce the desired consistency for injection. Most often this will be as thick as possible while still being able to be passed through a 16–18 gauge syringe. Because of the amorphous nature of the component solids in the paste, the material has markedly improved flow characteristics over prior art compositions. Flow characteristics of the resultant paste are toothpaste-like while prior art materials inherit a granular or oat meal-like consistency. The paste may be prepared before use, up to a period of several hours if held at room temperature and vaporization is minimized. The storage time may be extended by maintaining the paste at reduced temperatures in the range of 1–10° C. in the refrigerator provided steps are taken to minimize vaporization.

By selecting the appropriate amount of liquid to be added to the reactants, the viscosity of the bone substitution material paste may be adjusted according to need. The paste may be prepared either with an injectable or a formable consistency. Injectable consistency means as thick as possible while still capable of passing through a 16 to 18 gauge needle. Most often this will be a "toothpaste"-like consistency. Formable refers to consistency which allow the material to retain its shape. In the extreme case of a formable consistency, the paste will have the consistency of glazing putty or caulking compounds. The paste also may be prepared with just enough liquid to be both injectable and formable.

In some preferred embodiments (e.g., Examples 9–14, below), the reaction occurs slowly at room temperature, but is accelerated significantly at body temperature. This is particularly useful in a surgical situation, since the paste formed by mixing reactants with water remains injectable for a considerable period of time (up to several hours) while held at room temperature. Thus, at room temperature (ca. 22° C.) the paste hardens after a time greater than one hour and remains formable and/or injectable for longer than 10 minutes, and preferably longer than one hour and most preferably longer than three hours. Following injection at the implant site (ca. 37° C.), the paste hardens in less than about an hour, preferably in about 10–30 minutes.

In another embodiment of the invention, it is contemplated to incorporate bone regenerative proteins (BRP) into the amorphous calcium phosphate and acidic calcium phosphate mixture. BRPs have been demonstrated to increase the rate of bone growth and accelerate bone healing. A bone graft including nanocrystalline or poorly crystalline hydroxyapatite and BRP is expected to promote bone healing even more rapidly than a bone graft using the hydroxyapatite of the present invention alone. The efficacy of BRP is further enhanced by controlling the solubility of the nanocrystalline or poorly crystalline hydroxyapatite such that it dissolves at a rate that delivers BRP, calcium, and phosphorus at the optimum dosage for bone growth. Such a method of incorporating BRP would include, but not limited to, mixing a buffer solution containing BRP with its optimum pH that would maintain protein activity, instead of distilled water. Exemplary BRPs include, but are in no way limited to, Transforming Growth Factor-Beta, Cell-Attachment Factors, Endothelial Growth Factors, and Bone Morphogenetic Proteins. Such BRPs are currently being developed by Genetics Institute, Cambridge, Mass.; Genentech, Palo Alto, Calif.; and Creative Biomolecules, Hopkinton, Mass.

In another embodiment of the invention, it is contemplated to incorporate antibiotics or its agents into the amorphous calcium phosphate and its mixture. From a clinical sense, one of the major implication arising from a bone-graft surgery is a need to control the post-operative inflammation or infection. A bone graft including poorly crystalline hydroxyapatite and antibiotic(s) is expected to reduce the chances of local infection at the surgery site, contributing to infection-free, thus faster bone healing process. The efficacy of antibiotics is further enhanced by controlling the release of the poorly crystalline hydroxyapatite such that it dissolves at a rate that delivers antibiotic peptides or its active component at the most effective dosage to the tissue repair site. Exemplary antibiotics include, but are in no way limited to, Penicillin, Chlortetracycline hydrochloride (Aureomycine), Chloramphenicol and Oxytetracycline (Terramycine). Both antibiotics, mostly polypeptides, and bone regenerating proteins may be intermixed with the poorly crystalline hydroxyapatite material of the present invention, to locally deliver all or most of the necessary components in facilitating optimum condition for bone tissue repair.

EXAMPLES

The invention is further exemplified with reference to the following examples, which are presented for the purpose of illustration only and are not to be considered as limiting of the invention.

Example 1

This example describes the step-by-step preparation and methods to render relatively inert amorphous calcium phosphate solids into a highly reactive amorphous calcium phosphate of the present invention.

Solution A was prepared at room temperature by the rapid dissolution of 55 g $Na_2HPO_4 \cdot 7H_2O$ (sodium phosphate), 50 g NaOH (sodium hydroxide), 30 g $NaHCO_3$, (sodium bicarbonate) in 1.3 l of distilled water. $H_2O$ volumes in the range of 0.7 to 1.3 ml. have also been used. Solution B was prepared at room temperature by rapid dissolution of 43 g $Ca(NO_3)_2 \cdot 4H_2O$ (calcium nitrate tetrahydrate) in 0.5 l of distilled water.

The inert carbonated amorphous calcium phosphate was then prepared at room temperature by the rapid addition of solution B to rapidly stirring solution A. The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtrating funnel. The washed material was then collected using spatula and immersed into a liquid nitrogen in a 2.5 L container. Following the formation of hard frozen pieces, the container was transferred into a vacuum chamber for 24 hrs ($10^{-1}$ –$10^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form. Further, such elements or ions known to act as inhibitors of crystalline hydroxyapatite formation may be added into the solution in trace amounts. These may be, for example, Mg ions in the form of less than 1.0 g $MgCl_2.6H_2O$ (magnesium chloride), pyrophosphate ions in the form of less than 2 g $Na_4P_2O_7.10H_2O$ (sodium pyrophosphate).

An infrared spectrum of the inert amorphous material at this point in process is shown in FIG. 2a. This spectrum contains peaks characteristic of P—O groups (600 and 1000 $cm^{-1}$), $CO_3^{2-}$ group (1,420–1,450 $cm^{-1}$) with relatively large peak of O—H group (~3,550 $cm^{-1}$). X-ray diffraction pattern of the same material (FIG. 3a) show amorphous nature of the material as demonstrated by absence of any sharp peaks when the measurement of crystallinity is determined by taking ratio of coherent peaks to background.

The inert amorphous material described above was then made into a reactive form by heating for 60 minutes at 450° C. (±3° C.). The IR of the heated material is shown in FIG. 2b. This spectrum showed reduction of particular O—H and $CO_3^{2-}$ groups, indicating significant reduction of $H_2O$ and $CO_3^{2-}$ as $CO_2$ and $O_2$. In similarly prepared samples the carbon content was observed to drop approximately 60% with a total carbonate ratio decreasing from 1.56% to 0.5%. Note, however, that the amorphous nature of the material was not lost during this process, as demonstrated by the x-ray diffraction pattern shown in FIG. 3(b). The Ca/P ratio measurement of this material after the heat treatment was determined to be 1.575, using a method of quantitative electron microprobe analysis (FIG. 4). The overall morphological and ultrastructural properties of amorphous material is shown in FIG. 1, as seen under a transmission electron microscope. Note the "amorphous" appearance of the material with absence of sharp edges separating each granules with certain portion of the material to exhibit shapeless form (arrows). An extremely high specific surface area of 120 $m^2/g$, with an average pore size of approximately 130 Å was observed in this material.

Example 2

The preparation was conducted as described in Example 1 above, with the exception that the preparation of Solutions A and B was replaced by the following reactions. Solution A was prepared at room temperature by the rapid dissolution of 90.68 g of $Ca(NO_3)_2.4H_2O$ in 1.2 liter of carbonated distilled $H_2O$. Solution B was prepared by dissolving 40.57 g of $K_2HPO_4$ in 1.53 liters of distilled $H_2O$ containing 24 ml of 45 vol. % KOH solution. Chemical and physical properties of the product amorphous calcium phosphate resulting from this procedure were similar to those of the material prepared accordingly for Example 1.

Example 3

The preparation was conducted as described in Example 1 above, with the exception that the preparation of Solutions A and B were replaced by the following reactions. Solution A was prepared at room temperature by the rapid dissolution of 10.58 g of $Ca(NO_3)_2.6H_2O$ in 0.15 liters of carbonated distilled $H_2O$ at pH greater than 9.0, as adjusted by NaOH. Solution B was prepared by dissolving 7.8 g of $(NH_4)_2HPO_4$ in 0.35 liters of distilled $H_2O$. Chemical and physical properties of the product amorphous calcium phosphate resulting from this procedure were similar to those of the material prepared according to Examples 1 and 2.

Example 4

This example describes the preparation of bone substitute material of the invention.

The dicalcium phosphate dihydrate (DCPD) used in this example was prepared in the following manner. Solution A was prepared at room temperature by rapid dissolution of 10 g $H_9N_2O_4P$ (diammonium hydrogen phosphate) in 500 ml distilled water at a pH of 4.6–4.8. Solution B was prepared at room temperature by the rapid dissolution of 17.1 g $Ca(NO_3)_2.4H_2O$ (calcium nitrate tetrahydrate) in 250 ml distilled water. The dicalcium phosphate dihydrate was prepared at room temperature by the rapid addition of solution B to the stirring solution A. Immediately thereafter, the sample was filtered using filter paper (0.05 sq. m) with medium filter speed and a vacuum pressure of about $10^{-2}$ torr. The material formed a thin cake which was washed with about 2 liters of distilled water and then dried at room temperature for 24–72 hrs.

The reactive amorphous calcium phosphate material prepared from Examples 1, 2, or 3 was physically dry-mixed with dicalcium phosphate dihydrate ($CaHPO_4.2H_2O$) at 50:50 wt % using a mortar and pestle for 3–5 min. Water (1 ml/g of mixed material) was then added to the powder mixture to yield a paste-like consistency. The amount of $H_2O$ added varied, depending on whether a thick or thin paste was desired. The paste material was then placed in a moist tissue environment where upon reaching body temperature (37° C.), hardened into a solid mass without exothermic behavior. The hardening process could be delayed for several hours by placing it into a refrigerating temperature of 4° C. The hardened material was composed of nanometer-sized, poorly crystalline hydroxyapatite with an inherent solubility property that exceeded reported solubilities for a synthetic hydroxyapatite material. This is demonstrated in FIG. 5, where the concentration of calcium ions released into a controlled pH buffer solution over 24 hrs at 37° C., was significantly higher for the poorly crystalline HA material of the present invention (curve 50) than the standard crystalline hydroxyapatite material (curve 52).

Example 5

This example demonstrates the preparation of bone substitute material using materials having a selected particle size.

The reactive amorphous calcium phosphate material prepared from Examples 1, 2, or 3 was physically dry-mixed with dicalcium phosphate dihydrate ($CaHPO_4.2H_2O$) with a particle size of less than 100 μm at 50:50 wt. % using a SPEX 8510 laboratory mill for 2 min with a 8505 alumina ceramic grinding chamber, followed by sieving to a size of less than 100 μm. Water (1 ml/g of mixed material) was then added to the powder mixture to yield a paste-like consistency.

Example 6

Figure 5:
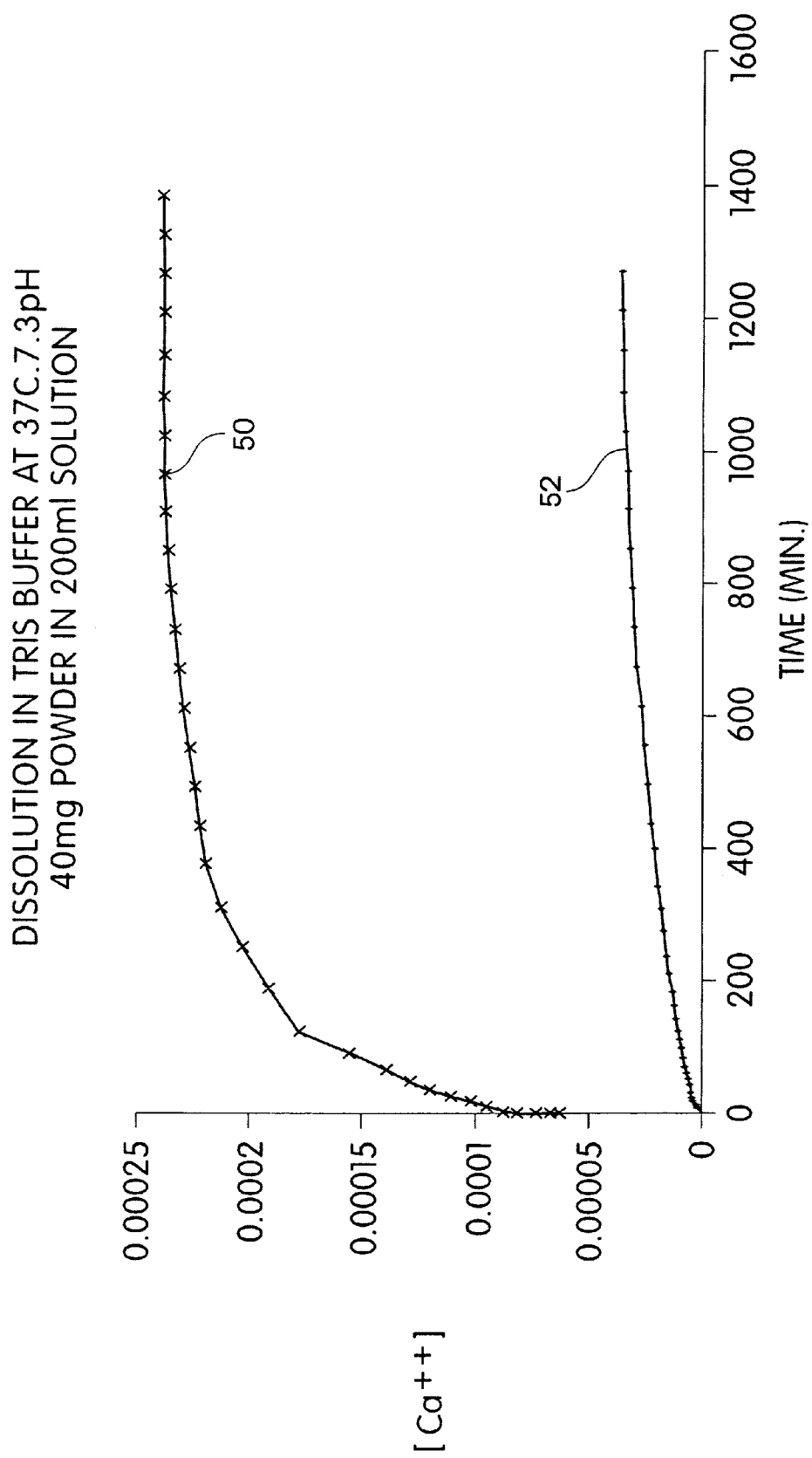
FIG. 5 is a solubility curve of a poorly crystalline hydroxyapatite product derived from amorphous calcium phosphate of the present invention when compared with a crystalline hydroxyapatite. Note the relative higher solubility of the material of the present invention versus a more crystalline form of hydroxyapatite, as measured by the amount of calcium ions released into solution at 37° C.

Reactive amorphous calcium phosphate material as prepared in Examples 1, 2, or 3 was dry-mixed with other calcium phosphate compounds, according to the method described in Example 4. These compounds included, but were not limited to: $Ca(PO_3)_2$ (calcium metaphosphates), $Ca_7(P_5O_{16})_2$ (heptacalcium phosphate), $Ca_2P_2O_7$ (calcium pyrophosphate), $Ca_3(PO_4)_2$ (tricalcium phosphates). The dry-mixture ratio was properly calculated to be between Ca/P ratios of 1.5–1.70, depending on the molar Ca/P ratio of the compound mixed with the reactive amorphous calcium. The resulting material was poorly crystalline hydroxyapatite solids with solubility properties same as shown in FIG. 5.

Example 7

This example describes the preparation of an injectable paste for the formation of poorly crystalline hydroxyapatite solid.

The dried mixed materials prepared according to Examples 4 or 6 were mixed with distilled $H_2O$ (2.3 ml/g). A paste was formed that could be easily shaped by hand or injected through a nozzle as small as 0.5 mm ID. The flowability increased after refrigerating the paste at 4° C. for 2–3 hrs.

The material could be stored in a paste form for about 12 hours at 4° C. in an air tight container without hardening.

Example 8

The crystalline content of the product bone substitute material was monitored by X-ray diffraction and I-R spectrometry.

FIG. 7a–d are the X-ray diffraction spectra of the reaction product between DCPD and the reactive amorphous calcium phosphate as described in Example 4. The reaction mixture was placed in a moist environment at 37° C. and examined by X-ray diffraction spectrometry at different times. X-ray scan conditions are (a) copper anode, (b) $\lambda=1.4540598$ Å, and (c) a scan range 20–35° at a step of 0.02° and step interval of 2 seconds. FIG. 8 shows the infrared spectra of dicalcium phosphate dihydrate (a), the activated ACP of the invention (b), and the poorly crystalline HA of the present invention (c).

Figure 7A:
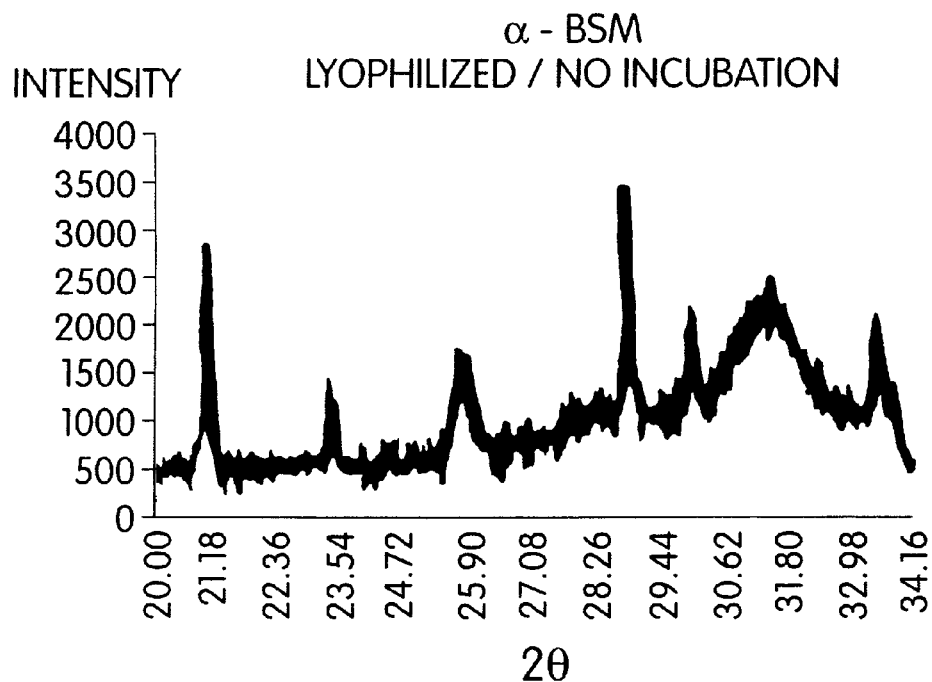
FIG. 7a–d are X-ray diffraction patterns tracking the progress of the reaction of a mixture of reactive amorphous calcium phosphate and dicalcium diphosphate to form a bone substitute material of the present invention.
Figure 7B:
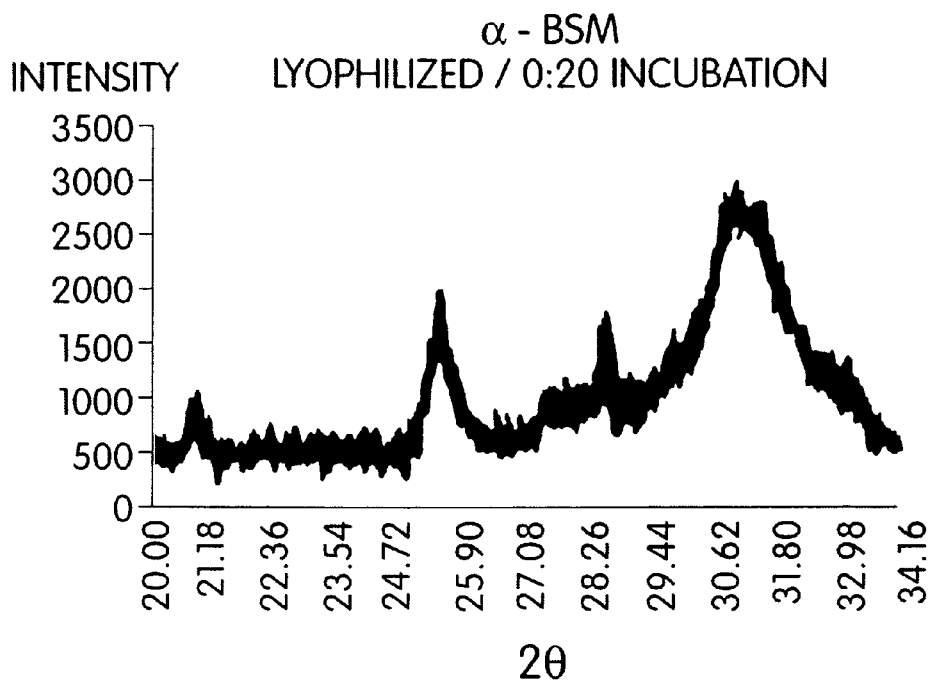
Figure 7C:
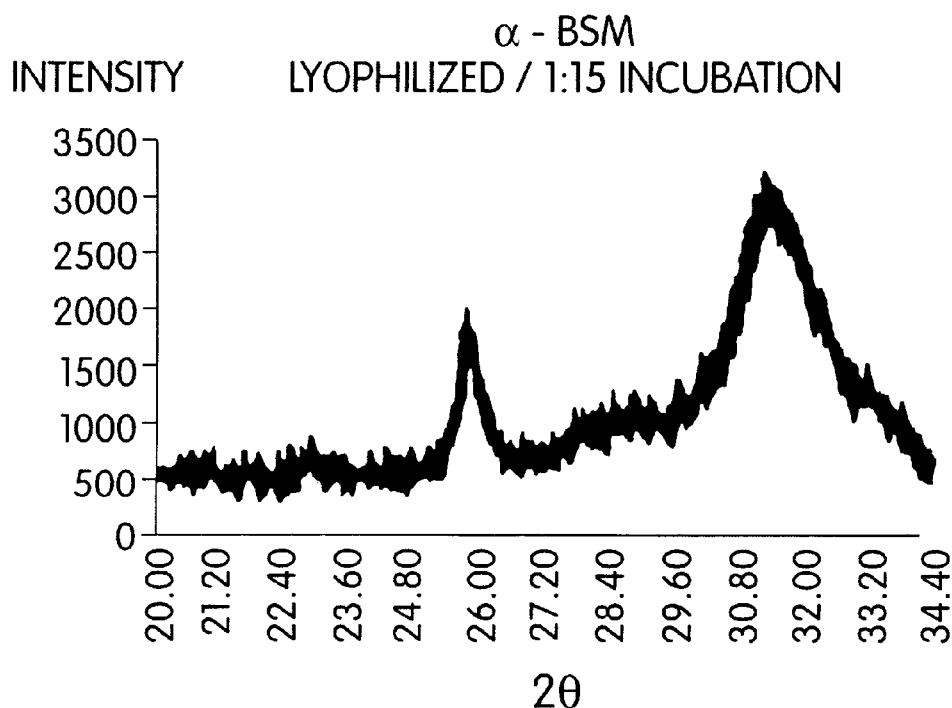
Figure 7D:
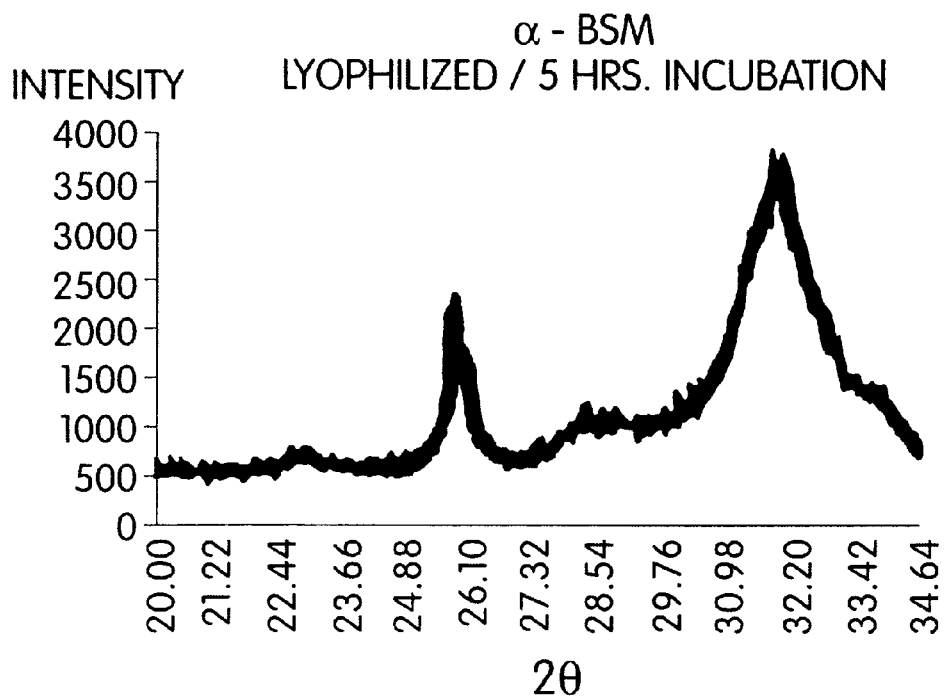
Figure 9:
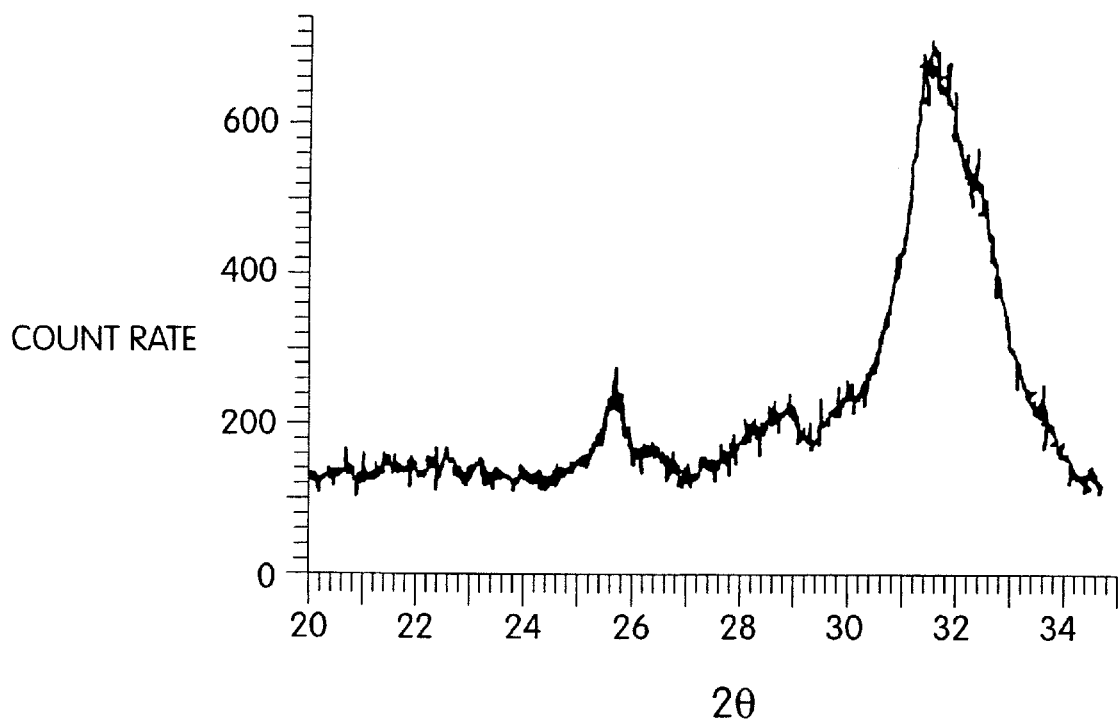
FIG. 9 is an X-ray diffraction pattern of naturally occurring bone.

Samples of FIGS. 7a–7d were incubated for 0, 20 min, 75 min and 5 hours, respectively. The samples were removed at the noted time and lyophilized to preserve chemical characteristics. FIG. 7a, taken at the start of the reaction, represents a combination of peaks attributable to the starting ACP and dicalcium diphosphate (see, FIG. 6 for component XRD patterns). The sharp peaks at ca. 20.25°, 23.5°, 29.5°, 30.75° and 34.2° for crystalline dicalcium diphosphate are readily observed. With increase in reaction time, the sharp crystalline peaks subside and wide (amorphous) peaks appear centered at 26°, 28.5°, 32.0° and 33.0°. It is interesting to note that there is no change in the spectra after 75 minutes of reaction, indicating that the reaction essentially complete in little more than one hour. The X-ray diffraction pattern of the bone substitute material of the invention (FIG. 7d) can be compared to that of naturally occurring bone, shown in FIG. 9. The two spectra are nearly identical, indicating the close biomimetry of the bone substitution material of the invention.

Examples 9–14

These examples demonstrate the effect of fluid volume on the consistency and reactivity of injectable paste to be used in the formation of bone substitute material. Each of the pastes were prepared as described in Example 7, above, and the consistency and rate of reaction at room temperature and 37° C. were determined. Observations are reported in Table 2.

TABLE 2

Formability, injectability and reactivity of one gram bone substitute material prepared with variable water volume.

| Example No. | water volume (mL) | formability | injectability | hardening time (min) (4° C./RT/37° C.) |
|---|---|---|---|---|
| 9 | 0.7 | – crumbles | – | —/—/— |
| 10 | 0.8* | +++ easily formed paste | + | >60/>60/30 |
| 11 | 0.9* | ++ toothpaste | ++ | >60/>60/30 |
| 12 | 1.0 | + liquid toothpaste | +++ | >60/>60/30 |

*Under some circumstances (e.g., evaporation) these samples may dry out somewhat over a period of one hour at room temperature. In such cases, additional water may be added to restore the original consistency.

Example 15

The purpose of this study was to evaluate the model as an analysis of efficacy of the implanted poorly crystalline hydroxyapatite calcium bone substitute material phosphate ceramic material of the invention when it was implanted into tibial bone surgically created defects of New Zealand White Rabbits.

I. Test Article and Animals

Test Article

The test article used was prepared as described in Example 7 with the exception that a buffer solution with optimum pH (saline) range for the protein or peptide bioactivity was used.

Animals

Seven adult male and female NZW rabbits (2.5–3.0 kg) were used in this study. Animals were obtained from Pine Acres Rabbitry/Farm. Animals were held in quarantine and acclimatization for a minimum of 10 days prior to the initiation of the study. They were evaluated by a veterinarian for general health prior to release from quarantine. Animals were individually housed in suspended stainless steel cages. Wood shavings were used in dropping pans under the cages. Animals were identified by a numbered ear tag or tattoo and by a corresponding cage card. All animals received the same treatment—one defect was placed in one tibia. Timepoints for evaluations were 0, 2, 4, and 8 weeks.

Surgical Procedure

After obtaining adequate anesthesia, using aseptic technique, an incision was made over the proximal tibia. The soft tissue was deflected away and the bone was exposed. Using a 5 mm trephine in a low speed dental handpiece drill with irrigation (0.9% physiologic saline) as needed, the bony disk was dissected free and the site was prepared for implantation. The bone substitute material paste form mixed α-BSM with saline, was placed into the defect. One sample per animal was administered using this method. The soft tissues were then closed in layers with 3–0 suture material. The animals were monitored and were given buprenorphine (0.02–0.05 mg/kg, s.c.) and cephalothin (20 mg./kg, s.c.) upon awakening. The analgesic and antibiotic were administered 2 times per day for five to seven days after surgery.

II. Experimental Observations

Clinical Observations and Radiographs

Clinical observations of the animals' general health and well-being with special regard to ambulation were performed at least weekly. Radiographs of the tibia were made at scheduled intervals including after surgery and at the time of necropsy.

The animals were allowed to heal for scheduled periods of time. The animals were anesthetized for tibial radiographs, which were taken every 2 weeks throughout the study. The radiographs were used to determine the duration of the study. Approximately every 2 weeks, 2 animals were sacrificed and the test sites were removed for histology. The animals were monitored daily to see if any changes in diet or behavior occurred. At the end of the study the animals were euthanized by an overdose of prescribed euthanasia solution. (ketamine HCl and Xylazine followed by saturated KCl)

Microscopic Pathology

The implantation sites were prepared as undecalcified and decalcified sections. Decalcified slides were prepared as plastic embedded light green basic fucsin 90 micron slides; undecalcified slides were stained with hematoxylin and eosin and Masson's trichrome. Slides were microscopically evaluated by a board certified veterinary pathologist (ACVP) with experience in laboratory animal pathology.

III. Results

Clinical Observations and Radiographs

Radiographs of the tibial defects showed increasing radiodensity with time.

Necropsy: The tibial defect sites appeared to be smaller with time. No excessive inflammation, other than that anticipated with any surgery, was observed grossly.

Microscopic Pathology

At 2 weeks, the bone substitute material calcium phosphate was still observed in the defect site as crystals both in the site and in local macrophages. Small spicules of trabecular bone were seen at the defect edges and in the defect site. By 4 weeks, few if any crystals of the device were visible; thicker trabecular bone was seen throughout the defect site. Specimens at 6 and 8 weeks had no evidence of the device; bone seen in the defect site was very thick trabecular to cortical type bone.

Example 16

Figure 8A:
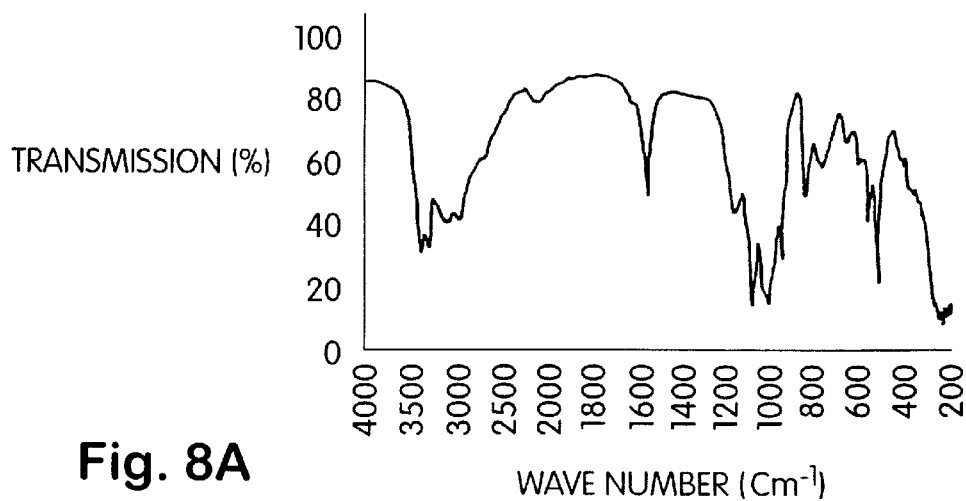
FIG. 8 is infrared spectra of (a) dicalcium phosphate dihydrate, (b) the activated ACP of the invention, and (c) the poorly crystalline HA of the present invention.
Figure 8B:
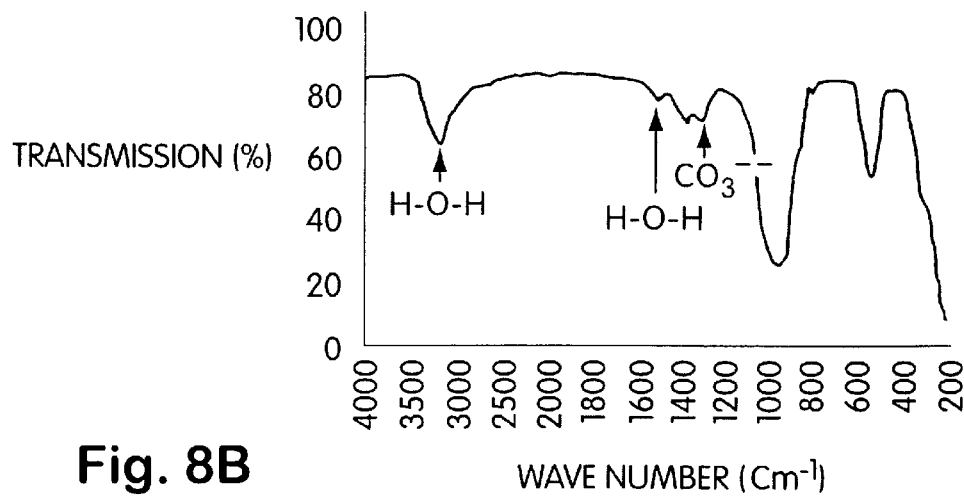
Figure 8C:
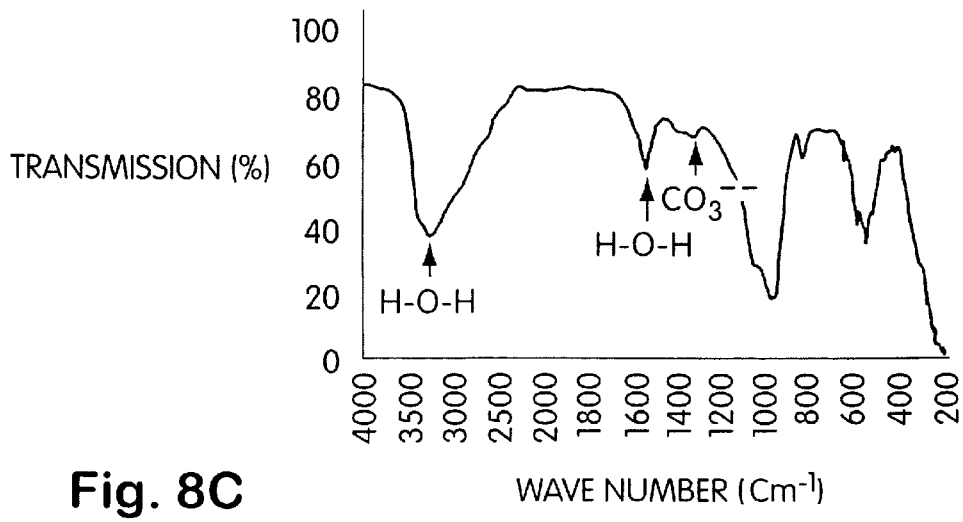

This example compares the infrared spectra of crystalline and amorphous precursors produced according to the examples and the final poorly crystalline HA produced by reacting similar precursors. FIG. 8a presents the IR spectrum of brushite (DCPD) prepared as described in Example 4; FIG. 8b presents the spectrum of ACP after heat treatment, prepared as described in Example 1; and FIG. 8c is the IR spectrum of poorly crystalline HA prepared as described in Example 4.

It will be understood that the objects set forth above, among those made apparent from the preceding description, are efficiently attained and, since certain changes may be made in carrying out the above process and in the composition set form without departing from the spirit and scope of the invention, it is intended that all matter contained in the above description and shown in the accompanying drawing (s) shall be interpreted as illustrative and not in a limiting sense.

It will be further understood that the following claims are intended to cover all of the generic and specific features of the invention herein described, and all statements of the scope of the invention which might be said to fall there between.

What is claimed is:

1. A formable paste, suitable for use as a bone substitution material, comprising:

a powder comprising a first calcium phosphate material having at least 90% amorphous character and an acidic second calcium phosphate material, the powder having a calcium to phosphorous molar ratio in the range of about 1.2 to 1.68; and a fluid in an amount to provide a formable or injectable consistency, said paste remaining injectable or formable for a time greater than about 60 minutes at about 22° C. and hardenable within about 30 minutes at about 37° C., said paste suitable for use as a bone substitute material.

2. The past of claim 1, wherein the mixture is injectable and formable at about 4° C. for a time up to about 12 hours.

3. The past of claim 1, wherein said paste converts into a poorly crystalline hydroxyapatite having the X-ray diffraction pattern of naturally occurring bone within five hours.

4. The paste of claim 1, wherein said paste converts into a poorly crystalline hydroxyapatite having the X-ray diffraction pattern of naturally occurring bone within seventy five minutes.

5. The paste of claim 1, wherein the paste is hardenable within about 10 to 30 minutes at about 37° C.

6. The paste of claim 1, wherein the material comprises a promoter selected to convert the calcium phosphate into a hydroxyapatitic calcium phosphate.

7. The paste of claim 1, wherein the fluid is selected from the group consisting of water, a physiologically acceptable pH-buffered solution, saline solution, serum and tissue culture medium.

8. The paste of claim 1, wherein the mixture comprises a second calcium phosphate powder which is amorphous or microcrystalline.

9. The paste of claim 1, wherein the second calcium phosphate powders selected from the group consisting of dicalcium phosphate dihydrate, calcium metaphosphate, heptacalcium phosphate, poorly crystalline hydroxyapatite, calcium pyrophosphates, octacalcium phosphate, and tricalcium phosphates.

10. The paste of claim 1 or 8, further comprising additional calcium sources.

11. The paste of claim 1 or 8, further comprising additional phosphate sources.

12. A method of promoting bone growth, comprising:

providing a paste, said paste comprising a calcium phosphate powder, said powder comprising a first calcium phosphate material having at least 90% amorphous character and an acidic second calcium phoshate material the powder having a calcium to phosphorous molar ratio in the range of about 1.2 to 1.68, and a fluid in an amount which provides a formable or injectable consistency, said paste remaining injectable or formable for a time greater than about 60 minutes at about 22° C.;

applying the paste to a site requiring bone growth: and allowing the paste to harden at the site within about 30 minutes.

13. The method of claim 12, further comprising:

addition of a bone regenerative protein or an antibiotic to the mixture prior to application.

14. The method of claim 12, wherein the fluid is selected from the group consisting of water, a physiologically acceptable pH-buffered solution, saline solution, serum and tissue culture medium.

15. The method of claims 12, wherein the paste is formed into the use shape outside the body.

16. The method paste of claim 12, wherein said paste converts into a poorly crystalline hydroxyapatite having the X-ray diffraction pattern of naturally occurring bone within five hours.

17. The method of claim 12, wherein said paste converts into a poorly crystalline hydroxyapatite having the X-ray diffraction pattern of naturally occurring bone within seventy five minutes.

18. The method of claim 12, wherein the paste is hardenable within about 10 to 30 minutes at about 37° C.

19. The method of claim 12, wherein the second calcium phosphate is selected from the group consisting of dicalcium phosphate dihydrate, calcium metaphosphate, heptacalcium phosphate, poorly crystalline hydroxyapatite, calcium pyrophosphates, octacalcium phosphate, and tricalcium phosphates.

20. The paste of claim 1, wherein the second calcium phosphate material is an acidic calcium phosphate having a pH between 5 and 7.

21. The method of claim 12, wherein the second calcium phosphate material is an acidic calcium phosphate having a pH between 5 and 7.

* * * * *